United States Patent [19]
Olson et al.

[11] Patent Number: 6,083,698
[45] Date of Patent: Jul. 4, 2000

[54] CANCER SUSCEPTIBILITY MUTATIONS OF BRCA1

[75] Inventors: Sheri Jon Olson, Falls Church, Va.; Tracy Staton Angelly, Gaithersburg; Tammy Lawrence, Laurel, both of Md.; Jennifer Lee Lescallett, Great Falls, Va.; Patricia Davis Murphy, Slingerlands, N.Y.; Antonette Preisinger Allen, Severn, Md.; Denise Bernadette Thurber, Silver Spring, Md.; Marga Belle White, Frederick, Md.; Bin Zeng, Indianapolis, Ind.; Lisa K. Sadzewicz, Laurel, Md.

[73] Assignee: Oncormed, Inc., Gaithersburg, Md.

[21] Appl. No.: 08/988,706

[22] Filed: Dec. 11, 1997

Related U.S. Application Data

[63] Continuation-in-part of application No. 08/533,472, Sep. 25, 1995, Pat. No. 5,756,294.

[51] Int. Cl.[7] ............................. C12Q 1/68; C12Q 19/34; C07H 21/04; C12N 15/85

[52] U.S. Cl. ........................ 435/6; 435/912; 435/320.1; 435/810; 536/23.5; 536/24.31; 536/24.33

[58] Field of Search ................................. 536/2.5, 24.31, 536/24.33; 435/6, 91.2, 320, 810; 935/77.78

[56] References Cited

U.S. PATENT DOCUMENTS

| | | | |
|---|---|---|---|
| 5,700,637 | 12/1997 | Southern | 435/6 |
| 5,756,294 | 5/1998 | White et al. | 435/6 |

*Primary Examiner*—Stephanie Zitomer
*Attorney, Agent, or Firm*—Baker Botts

[57] ABSTRACT

New mutations have been found in the BRCA1 gene. The mutations are located at nucleotide numbers 421-2, 815, 903, 926, 1506, 2034, 2428, 3888, 3904, 4164, 4643, 5053, 5150, 5210, or 5396+40 of the gene sequence of BRCA1. A process for identifying a sequence variation in a BRCA1 polynucleotide sequence is disclosed. The identification process includes allele specific sequence-based assays of known sequence variations. The methods can be used for efficient, and accurate detection of a mutation in a test BRCA1 gene sample.

91 Claims, No Drawings

```
                            SEQUENCE LISTING (1) GENERAL INFORMATION:

(iii) NUMBER OF SEQUENCES: 55

(2) INFORMATION FOR SEQ ID NO:1:

(i) SEQUENCE CHARACTERISTICS:
           (A) LENGTH: 23 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
           (A) ORGANISM: HOMO SAPIENS
           (B) STRAIN: BRCA1

(xi) SEQUENCE DESCRIPTION: SEQ ID NO:1:

CACAACAAAG AGCATACATA GGG                                                  23

(2) INFORMATION FOR SEQ ID NO:2:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
           (A) ORGANISM: HOMO SAPIENS
           (B) STRAIN: BRCA1

(xi) SEQUENCE DESCRIPTION: SEQ ID NO:2:

TCGGGTTCAC TCTGTAGAAG                                                      20

(2) INFORMATION FOR SEQ ID NO:3:

(i) SEQUENCE CHARACTERISTICS:
           (A) LENGTH: 17 base pairs
           (B) TYPE: nucleic acid
           (C) STRANDEDNESS: single
           (D) TOPOLOGY: linear
```

```
        (ii) MOLECULE TYPE: other nucleic acid
             (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:3:

TATTTTACAG ATGCAAA                                                          17

(2) INFORMATION FOR SEQ ID NO:4:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:4:

TATTTTACGA TGCAAAC                                                          17

(2) INFORMATION FOR SEQ ID NO:5:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:5:

CCAAGGTGTA TGAAGTATGT                                                       20

(2) INFORMATION FOR SEQ ID NO:6:

(i) SEQUENCE CHARACTERISTICS:
             (A) LENGTH: 19 base pairs
             (B) TYPE: nucleic acid
             (C) STRANDEDNESS: single
             (D) TOPOLOGY: linear
```

(ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:6:

GTTATGTTGG CTCCTTGCT                                                        19

(2) INFORMATION FOR SEQ ID NO:7:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: other nucleic acid
            (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:7:

GACGGATGTA ACAAATA                                                          17

(2) INFORMATION FOR SEQ ID NO:8:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: other nucleic acid
            (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:8:

GAGACGGATA ACAAATA                                                          17

(2) INFORMATION FOR SEQ ID NO:9:

(i) SEQUENCE CHARACTERISTICS:
             (A) LENGTH: 27 base pairs
             (B) TYPE: nucleic acid
             (C) STRANDEDNESS: single
             (D) TOPOLOGY: linear

```
    (ii) MOLECULE TYPE: other nucleic acid
         (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
         (A) ORGANISM: HOMO SAPIENS
         (B) STRAIN: BRCA1

(xi) SEQUENCE DESCRIPTION: SEQ ID NO:9:

CATGTGGAGC CATGTGGCAC AAATACT                                             27

(2) INFORMATION FOR SEQ ID NO:10:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
         (A) ORGANISM: HOMO SAPIENS
         (B) STRAIN: BRCA1

(xi) SEQUENCE DESCRIPTION: SEQ ID NO:10:

CATGTGGAGC CATGTGGAGC CATGTGG                                             27

(2) INFORMATION FOR SEQ ID NO:11:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
         (A) ORGANISM: HOMO SAPIENS
         (B) STRAIN: BRCA1

(xi) SEQUENCE DESCRIPTION: SEQ ID NO:11:

ACTGTTAGGT TCTGATGACT                                                     20

(2) INFORMATION FOR SEQ ID NO:12:

(i) SEQUENCE CHARACTERISTICS:
         (A) LENGTH: 20 base pairs
         (B) TYPE: nucleic acid
         (C) STRANDEDNESS: single
         (D) TOPOLOGY: linear
```

```
    (ii) MOLECULE TYPE: other nucleic acid
         (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
         (A) ORGANISM: HOMO SAPIENS
         (B) STRAIN: BRCA1

(xi) SEQUENCE DESCRIPTION: SEQ ID NO:12:

ATCATTTCAG GAGTCTTTTG                                                  20

(2) INFORMATION FOR SEQ ID NO:13:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
         (A) ORGANISM: HOMO SAPIENS
         (B) STRAIN: BRCA1

(xi) SEQUENCE DESCRIPTION: SEQ ID NO:13:

TATTTGGGAA AACCTAT                                                     17

(2) INFORMATION FOR SEQ ID NO:14:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
         (A) ORGANISM: HOMO SAPIENS
         (B) STRAIN: BRCA1

(xi) SEQUENCE DESCRIPTION: SEQ ID NO:14:

TATTTGGGAA ACCTATC                                                     17

(2) INFORMATION FOR SEQ ID NO:15:

(i) SEQUENCE CHARACTERISTICS:
         (A) LENGTH: 22 base pairs
         (B) TYPE: nucleic acid
         (C) STRANDEDNESS: single
         (D) TOPOLOGY: linear
```

(ii) MOLECULE TYPE: other nucleic acid
             (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:15:

GTATAAGCAA TATGGAACTC GA                                                     22

(2) INFORMATION FOR SEQ ID NO:16:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:16:

TTAAGTTCAC TGGTATTTGA ACA                                                    23

(2) INFORMATION FOR SEQ ID NO:17:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:17:

GTACTGAATT GCAAATT                                                           17

(2) INFORMATION FOR SEQ ID NO:18:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: other nucleic acid
            (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
            (A) ORGANISM: HOMO SAPIENS
            (B) STRAIN: BRCA1

(xi) SEQUENCE DESCRIPTION: SEQ ID NO:18:

GTACTGAACT GCAAATT                                                         17

(2) INFORMATION FOR SEQ ID NO:19:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
            (A) ORGANISM: HOMO SAPIENS
            (B) STRAIN: BRCA1

(xi) SEQUENCE DESCRIPTION: SEQ ID NO:19:

TGGAACAACC ATGAATTAGT C                                                    21

(2) INFORMATION FOR SEQ ID NO:20:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
            (A) ORGANISM: HOMO SAPIENS
            (B) STRAIN: BRCA1

(xi) SEQUENCE DESCRIPTION: SEQ ID NO:20:

CAGTATTTCA TTGGTAC                                                         17

(2) INFORMATION FOR SEQ ID NO:21:

(i) SEQUENCE CHARACTERISTICS:
            (A) LENGTH: 17 base pairs
            (B) TYPE: nucleic acid
            (C) STRANDEDNESS: single
            (D) TOPOLOGY: linear

```
        (ii) MOLECULE TYPE: other nucleic acid
             (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:21:

CAGTATTTAA TTGGTAC                                                    17

(2) INFORMATION FOR SEQ ID NO:22:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:22:

TGGCTGCCCA GGAAGTATG                                                  19

(2) INFORMATION FOR SEQ ID NO:23:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:23:

AACCAGAATA TCTTTATGTA GGA                                             23

(2) INFORMATION FOR SEQ ID NO:24:

(i) SEQUENCE CHARACTERISTICS:
             (A) LENGTH: 17 base pairs
             (B) TYPE: nucleic acid
             (C) STRANDEDNESS: single
             (D) TOPOLOGY: linear
```

(ii) MOLECULE TYPE: other nucleic acid
             (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:24:

GATAGGTGGT ACATGCA                                                     17

(2) INFORMATION FOR SEQ ID NO:25:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:25:

GATAGGTGAT ACATGCA                                                     17

(2) INFORMATION FOR SEQ ID NO:26:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:26:

AATTCTTAAC AGAGACCAGA AC                                               22

(2) INFORMATION FOR SEQ ID NO:27:

(i) SEQUENCE CHARACTERISTICS:
             (A) LENGTH: 22 base pairs
             (B) TYPE: nucleic acid
             (C) STRANDEDNESS: single
             (D) TOPOLOGY: linear

```
    (ii) MOLECULE TYPE: other nucleic acid
         (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
         (A) ORGANISM: HOMO SAPIENS
         (B) STRAIN: BRCA1

(xi) SEQUENCE DESCRIPTION: SEQ ID NO:27:

AAAACTCTTT CCAGAATGTT GT                                              22

(2) INFORMATION FOR SEQ ID NO:28:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
         (A) ORGANISM: HOMO SAPIENS
         (B) STRAIN: BRCA1

(xi) SEQUENCE DESCRIPTION: SEQ ID NO:28:

ACAGAAAGGG TCAACAA                                                    17

(2) INFORMATION FOR SEQ ID NO:29:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
         (A) ORGANISM: HOMO SAPIENS
         (B) STRAIN: BRCA1

(xi) SEQUENCE DESCRIPTION: SEQ ID NO:29:

ACAGAAAGGT CAACAAA                                                    17

(2) INFORMATION FOR SEQ ID NO:30:

(i) SEQUENCE CHARACTERISTICS:
         (A) LENGTH: 21 base pairs
         (B) TYPE: nucleic acid
         (C) STRANDEDNESS: single
         (D) TOPOLOGY: linear
```

```
        (ii) MOLECULE TYPE: other nucleic acid
             (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:30:

GGCTCTTTAG CTTCTTAGGA C                                              21

(2) INFORMATION FOR SEQ ID NO:31:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:31:

GAGACCATTT TCCCAGCATC                                                20

(2) INFORMATION FOR SEQ ID NO:32:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:32:

GTTTGTGTGT GAACGGA                                                   17

(2) INFORMATION FOR SEQ ID NO:33:

(i) SEQUENCE CHARACTERISTICS:
             (A) LENGTH: 17 base pairs
             (B) TYPE: nucleic acid
             (C) STRANDEDNESS: single
             (D) TOPOLOGY: linear
```

(ii) MOLECULE TYPE: other nucleic acid
              (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
              (A) ORGANISM: HOMO SAPIENS
              (B) STRAIN: BRCA1

(xi) SEQUENCE DESCRIPTION: SEQ ID NO:33:

GTTTGTGTGG AACGGAC                                                          17

(2) INFORMATION FOR SEQ ID NO:34:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
              (A) ORGANISM: HOMO SAPIENS
              (B) STRAIN: BRCA1

(xi) SEQUENCE DESCRIPTION: SEQ ID NO:34:

ATATGACGTG TCTGCTCCAC                                                       20

(2) INFORMATION FOR SEQ ID NO:35:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
              (A) ORGANISM: HOMO SAPIENS
              (B) STRAIN: BRCA1

(xi) SEQUENCE DESCRIPTION: SEQ ID NO:35:

GGGAATCCAA ATTACACAGC                                                       20

(2) INFORMATION FOR SEQ ID NO:36:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: other nucleic acid
             (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:36:

CCACTCTGTA TTCCACTCCC CTTTGCAG                                              28

(2) INFORMATION FOR SEQ ID NO:37:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:37:

CCACTCTGTA TTCCACTCTG TATTCCAC                                              28

(2) INFORMATION FOR SEQ ID NO:38:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:38:

GTGTAGAACG TGCAGGATTG                                                       20

(2) INFORMATION FOR SEQ ID NO:39:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: other nucleic acid
        (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA1

(xi) SEQUENCE DESCRIPTION: SEQ ID NO:39:

TCGCCTCATG TGGTTTTA                                                          18

(2) INFORMATION FOR SEQ ID NO:40:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA1

(xi) SEQUENCE DESCRIPTION: SEQ ID NO:40:

CACTTTAACT AATCTAA                                                           17

(2) INFORMATION FOR SEQ ID NO:41:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
        (A) ORGANISM: HOMO SAPIENS
        (B) STRAIN: BRCA1

(xi) SEQUENCE DESCRIPTION: SEQ ID NO:41:

CACTTTAACA ATCTAAT                                                           17

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
             (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:42:

GAAGTAATTG TAAGCATCCT                                                        20

(2) INFORMATION FOR SEQ ID NO:43:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:43:

CATTTTGTTT CCTCACTAAG                                                        20

(2) INFORMATION FOR SEQ ID NO:44:

(i) SEQUENCE CHARACTERISTICS:
             (A) LENGTH: 16 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:44:

TATTATCATT GAAGAA                                                            16

(2) INFORMATION FOR SEQ ID NO:45:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:45:

TTATTATAAT TGAAGAA                                                              17

(2) INFORMATION FOR SEQ ID NO:46:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:46:

GCAAAAGCGT CCAGAAAGAG                                                           20

(2) INFORMATION FOR SEQ ID NO:47:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:47:

AGTCTTCCAA TTCACTGCAC                                                           20

(2) INFORMATION FOR SEQ ID NO:48:

(i) SEQUENCE CHARACTERISTICS:
             (A) LENGTH: 14 base pairs
             (B) TYPE: nucleic acid
             (C) STRANDEDNESS: single
             (D) TOPOLOGY: linear

```
        (ii) MOLECULE TYPE: other nucleic acid
             (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:48:

GAACACAGGA GAAT                                                            14

(2) INFORMATION FOR SEQ ID NO:49:

(i) SEQUENCE CHARACTERISTICS:
             (A) LENGTH: 14 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:49:

TAAGAACACA GGAG                                                            14

(2) INFORMATION FOR SEQ ID NO:50:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
             (A) ORGANISM: HOMO SAPIENS
             (B) STRAIN: BRCA1

(xi) SEQUENCE DESCRIPTION: SEQ ID NO:50:

GAAAAGTATC AGGGTAG                                                         17

(2) INFORMATION FOR SEQ ID NO:51:

(i) SEQUENCE CHARACTERISTICS:
             (A) LENGTH: 17 base pairs
             (B) TYPE: nucleic acid
             (C) STRANDEDNESS: single
             (D) TOPOLOGY: linear
```

```
    (ii) MOLECULE TYPE: other nucleic acid
         (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
         (A) ORGANISM: HOMO SAPIENS
         (B) STRAIN: BRCA1

(xi) SEQUENCE DESCRIPTION: SEQ ID NO:51:

GAAAAGTAGC AGGGTAG                                                17

(2) INFORMATION FOR SEQ ID NO:52:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
         (A) ORGANISM: HOMO SAPIENS
         (B) STRAIN: BRCA1

(xi) SEQUENCE DESCRIPTION: SEQ ID NO:52:

CTAAGAACAC AGAGGAGAA                                              19

(2) INFORMATION FOR SEQ ID NO:53:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PRIMER"

(iii) HYPOTHETICAL: NO (iv) ANTI-SENSE: NO (v) FRAGMENT TYPE: internal (vi) ORIGINAL SOURCE:
         (A) ORGANISM: HOMO SAPIENS
         (B) STRAIN: BRCA1

(xi) SEQUENCE DESCRIPTION: SEQ ID NO:53:

CTAGCTGTGT GAAGGACT                                               18

(2) INFORMATION FOR SEQ ID NO:54:

(i) SEQUENCE CHARACTERISTICS:
         (A) LENGTH: 17 base pairs
         (B) TYPE: nucleic acid
         (C) STRANDEDNESS: single
         (D) TOPOLOGY: linear
```

```
    (ii) MOLECULE TYPE: other nucleic acid
         (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
         (A) ORGANISM: HOMO SAPIENS
         (B) STRAIN: BRCA1

(xi) SEQUENCE DESCRIPTION: SEQ ID NO:54:

AAGAGGAACG GGCTTGG                                                         17

(2) INFORMATION FOR SEQ ID NO:55:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "PROBE"

(iii) HYPOTHETICAL: NO (iv) ANTI-SENSE: NO (v) FRAGMENT TYPE: internal (vi) ORIGINAL SOURCE:
         (A) ORGANISM: HOMO SAPIENS
         (B) STRAIN: BRCA1

(xi) SEQUENCE DESCRIPTION: SEQ ID NO:55:

AAGAGGACCG GGCTTGG                                                         17
```

CANCER SUSCEPTIBILITY MUTATIONS OF BRCA1

This application is a continuation-in-part application of U.S. Ser. No. 08/533,472, filed Sep. 25, 1995, now U.S. Pat. No. 5,756,294, the contents of which are incorporated by reference.

FIELD OF THE INVENTION

This invention relates to the breast cancer succepibility gene BRCA1. More specifically, this invention detects germline mutations of the BRCA1 gene that are associated with a predisposition to breast, ovarian and asociated cancers. Methods and reagents for detecting the presence of these mutations are included.

BACKGROUND OF THE INVENTION

It has been estimated that about 5–10% of breast cancer is inherited Rowell, et al., *American Journal of Human Genetics*, 55:861–865 (1994). Located on chromosome 17, BRCA1 is the first gene identified conferring increased risk for breast and ovarian cancer. Miki et al., *Science*, 266:66–71 (1994). Mutations in this tumor suppressor gene account for roughly 45% of inherited breast cancer and 80–90% of families with increased risk of early onset breast and ovarian cancer. Easton et al., *American Journal of Human Genetics*. 52:678–701 (1993).

The location of one or more mutations in the BRCA1 region of chromosome 17 provides a promising approach to reducing the high incidence and mortality associated with breast and ovarian cancer through the early detection of women at high risk. These women, once identified, can be targeted for more aggressive prevention programs. These mutations are also associated with an increased risk of ovarian cancer, prostrate cancer and pancreatic cancer. Screening is carried out by a variety of methods which include karyotyping, probe binding and DNA sequencing.

In DNA sequencing technology, genomic DNA is extracted from whole blood and the coding regions of the BRCA1 gene are amplified using the polymerase chain reaction (PCR). Each of the coding regions is sequenced completely and the results are compared to the normal DNA sequence of the gene (GENBANK Accession Numbers: U14680 and U15595). Many mutations and several polymorphisms have already been reported in the BRCA1 gene. Shattuck-Eidens, et al., *Journal of the American Medical Association*, 273: 535–541 (1995).

The BRCA1 gene (GENBANK Accession Numbers: U14680 and 15595) is divided into 24 separate exons. Exons 1 and 4 are noncoding, in that they are not part of the final functional BRCA1 protein product. The BRCA1 coding region spans roughly 5600 base pairs (bp). Each exon consists of 200–400 bp, except for exon 11 which contains about 3600 bp. To sequence the coding region of the BRCA1 gene, each exon is amplified separately and the resulting PCR products are sequenced in the forward and reverse directions. Because exon 11 is so large, it was divided it into multiple overlapping PCR fragments.

There is a need in the art to identify mutations in the BRCA1 gene. Identification of mutations of the BRCA1 gene and protein would allow more widespread diagnostic screening for hereditary breast and ovarian cancer than is currently possible.

Many mutations and normal polymorphisms have already been reported in the BRCA1 gene. A world wide web site has been built to facilitate the detection and characterization of alterations in breast cancer susceptibility genes. Such mutations in BRCA1 can be accessed through the Breast Cancer Information Core at: HTTP://www.nchgr.nih.gov/dir/lab_transfer/bic.

While mutations occur throughtout the BRCA1 gene, there is a need for a high sample number (throughput), sensitivity, accuracy and cost effectiveness. Identification of mutations of the BRCA1 gene would allow more widespread diagnostic screening for hereditary breast and ovarian cancer than is currently possible and permit identification of functional areas deduced from the mutational spectrum observed.

SUMMARY OF THE INVENTION

The present invention is based on the discovery of fifteen mutations in the BRCA1 gene sequence which is associated with susceptibility to and development of breast and ovarian cancer. Specifically, mutations located at nucleotide numbers 421-2, 815, 926, 1506, 2034, 2428, 4643, 5053, 5210, 5396+40, 5150, 3904, 3888, 903 and 4164, have been discovered.

It is an object of the invention to provide a method for determining a predisposition or higher susceptibility to breast, ovarian and other cancers.

It is another object of the invention to provide primers for detecting and amplifying a region of DNA which contains the BRCA1 mutations.

It is another object of the invention to provide probes for detecting a region of DNA which contains the BRCA1 mutations.

It is a further object of the invention to provide a method of characterizing and classifying a tumor and determining a therapy dependant upon the type of mutation(s) present.

It is also an object of the present invention to provide a mutant BRCA1 gene and expressed mutant protein for drug development, gene therapy and other uses to prevent or amelorate the effects of or resulting from the mutant BRCA1 gene.

DETAILED DESCRIPTION OF THE PREFERRED EMBODIMENTS

For defining the present invention, the following nomenclature is used to describe the mutations and polymorphisms due to an inconsistency in the published literature. Beaudet et al, *Human Mutations*, 2: 245–248 (1993), Antonarakis et al, *Human Mutations*, 4: 166 (1994), Cotton, *Human Mutations*, 8: 197–202 (1996), and Beutler et al, *Human Mutations*, 8: 203–206 (1996). In defining the mutation, the number indicates the nucleotide position corresponding to the BRCA1 gene sequence where the mutation first occurs. Other BRCA1 sequences which are polymorphisms or genetic variations of BRCA1 may be used, in which a corresponding mutation at the corresponding nucleotide number is present. See U.S. Pat. No. 5,654,155 where the inventors have discovered other normal BRCA1 gene sequences. The invention is equally applicable to all of the normal BRCA1 sequences. Also note Shattuck-Eidens, et al., *Journal of the American Medical Association*, 287: 1242–1250 (1997) for some of the other haplotypes of BRCA1.

When the mutation is in an intron, the nucleotide number + or − a number of bases is given as the coding sequence numbering does not include introns. Insertion mutations are indicated by "ins" and deletion mutations are indicated by "del". The letters following "ins" or "del" refer to the nucleotide(s) which were inserted or deleted. When more than two nucleotides are inserted or deleted, the number of nucleotides is listed. When the mutation results in one nucleotide being substituted for another, the letter to the left of the number is the nucleotide which is normally found and the number to the right is the nucleotide found in the mutations of the present invention.

The first mutation is referred to as IVS6-2delA. This mutation causes deletion of the A in the intron two nucleotides upstream from nucleotide number 421. The exact effect of this mutation is unknown but appears to be in the splice site region. Any change in splicing of the exons may change the amino acid sequence and have a negative affect on the biological activity of the BRCA1 protein.

The second mutation is referred to as 815delTG. This mutation deletes TG at nucleotide number 815 causing a frameshift mutation and forming an in-frame stop codon at codon 236. This mutation results in a truncated (as measured by gel electrophoresis), and most likely, non-functional protein.

The third mutation is referred to as 926ins10. This mutation inserts the ten bases CATGTGGAGC at nucleotide number 926 causing a frameshift mutation and forming an in-frame stop codon at codon 289. This mutation is therefore predicted to result in a truncated, and most likely, non-functional protein.

The fourth mutation is referred to as 1506delA. This mutation deletes an A at nucleotide number 1506 causing a frameshift mutation and forming an in-frame stop codon at codon 474. This mutation results in a truncated (as measured by gel electrophoresis), and most likely, non-functional protein.

The fifth mutation is a polymorphism referred to as T2034C. This mutation is actually a polymorphism which substitutes a C for a T at nucleotide number 2034 causing codon 639 to remain coding for leucine. While the change is conservative, is is unclear whether this change affects the secondary structure of mRNA or some other effect leading to an altered level of expression or splicing. For the purposes of this application, this polymorphism is sometimes referred to as a mutation.

The sixth mutation is referred to as C2428A. This mutation substitutes A for C at nucleotide number 2428 causing a stop codon to be formed at codon 770 instead of serine. This mutation results in a truncated (as determined by gel electrophoresis), and most likely, non-functional protein.

The seventh mutation is referred to as G4643A. This mutation substitutes an A for G at nucleotide number 4643 causing a stop codon to be formed at codon 1508 instead of tryptophan. This mutation is therefore predicted to result in a truncated, and most likely, non-functional protein.

The eighth mutation is referred to as 5053delG. This mutation deletes a G at nucleotide number 5053 causing a frameshift mutation and forming an in-frame stop codon at codon 1657. This mutation is therefore predicted to result in a truncated, and most likely, non-functional protein.

The ninth mutation is referred to as 5210delT. This mutation deletes a T at nucleotide number 5210 causing a frameshift mutation and forming an in-frame stop codon at codon 1701. This mutation is therefore predicted to result in a truncated, and most likely, non-functional protein.

The tenth mutation is referred to as IVS20+40ins12. This mutation inserts the twelve nucleotides CCACTCTGTATT at a nucleotide location forty bases downstream from nucleotide number 5396. The exact effect of this mutation is unknown but appears to be in the splice site region. Any change in the introns may have a negative affect the biological activity of or the level of BRCA1 protein. This mutation is believed to represent an actual family mutation.

The eleventh mutation is referred to as 5150delT. This mutation deletes a T at nucleotide number 5150 causing a frameshift mutation and forming an in-frame stop codon at codon 1679. This mutation is therefore predicted to result in a truncated, and most likely, non-functional protein.

The twelvth mutation is referred to as C3904A. This mutation substitutes an A for C at nucleotide number 3904 causing a stop codon to be formed at codon 1262 instead of serine. This mutation results in a truncated (as determined by gel electrophoresis), and most likely, non-functional protein.

The thirteenth mutation is referred to as 3888delGA. This mutation deletes GA at nucleotide number 3888 causing a frameshift mutation and forming an in-frame stop codon at codon 1265. This mutation results in a truncated (as determined by gel electrophoresis), and most likely, non-functional protein.

The fourteenth mutation is referred to as T903G. This mutation substitutes a G for T at nucleotide number 903 causing a stop codon to be formed at codon 261 instead of tyrosine. This mutation is therefore predicted to result in a truncated, and most likely, non-functional protein.

The fifteenth mutation is referred to as A4164C. This mutation substitutes a C for A at nucleotide number 4164 causing codon 1349 to change from threonine to proline. This mutation is therefore predicted to result in BRCA1 protein with a different amino acid sequence. Any amino acid sequence change may have a harmful effect on the biological activity of the BRCA1 protein. It should be particularly noted that proline and threonine are nor related amino acids and that proline may change the three dimentional protein structure by inducing a bend.

Useful DNA molecules according to the present invention are those which will specifically hybridize to BRCA1 sequences in the region of the IVS6-2delA, 815delTG, 926ins10, 1506delA, T2034C, C2428A, G4643A, 5053delG, 5210delT, IVS20+40ins12, 5150delT, C3904A, 3888delGA, T903G or A4164C mutation. Typically these DNA molecules are 16 to 27 nucleotides in length (longer for large insertions) and have the nucleotide sequence corresponding to the region of the mutations at their respective nucleotide locations on the BRCA1 sequence. Such molecules can be labeled, according to any technique known in the art, such as with radiolabels, fluorescent labels, enzymatic labels, sequence tags, biotin, other ligands, etc.

According to another aspect of the invention, the DNA molecules contain one or more of the specific mutations. Generally it is preferred for each DNA probe to encompass only one mutation. Such molecules may be labeled and can be used as allele-specific oligonucleotide probes to detect the mutation of interest.

Polynucleotide containing biological samples, such as blood, can be tested to determine whether the BRCA1 gene contains one of the specific mutations listed above. To amplify the BRCA1 gene, one may use PCR using primers which hybridize to the ends of the exons or to the introns flanking the exons. To detect mutations in the introns, primers amplifying the introns, especially the regions adjacent to the exons, may be used. In the situation of exon 11, the exon is so large that using plural pairs of primers to amplify overlapping regions is preferred. Such was actually used in the Examples below.

Amplification may also be performed by a number of other techniques such as by cloning the gene or gene fragments, and linking the BRCA1 gene or fragments thereof in the sample to a vector. "Shot gun" cloning is particularly preferred. For the purposes of this application, a vector may be any polynucleotide containing system which induces replication such as a plasmid, cosmid, virus, transposon, or portions thereof.

In one embodiment of the invention a pair of isolated oligonucleotide primers are provided.

BRCA1 -IVS6F 5'CAC AAC AAA GAG CAT ACA TAG GG 3', SEQ ID NO:1

BRCA1-IVS6R 5'TCG GGT TCA CTC TGT AGA AG 3', SEQ ID NO:2

The designation BRCA1-IVS6 refers to a sequence in intervening sequence 6 of the BRCA1 gene. F and R refer to forward and reverse. The oligonucleotide primers are useful in directing amplification of a target polynucleotide prior to sequencing. These unique BRCA1 intron 6 oligonucleotide primers were used to scan the BRCA1 gene to find the mutation. From the sequence information, the probes were designed and produced for the mutation based upon identification of the IVS6-2delA mutation.

In another embodiment of the invention a pair of isolated allele specific oligonucleotide probes are provided.

5'TAT TTT ACA GAT GCA AA 3', SEQ ID NO:3

5'TAT TTT ACG ATG CAA AC 3', SEQ ID NO:4

These allele specific oligonucleotides are useful in diagnosis of a subject at risk of having breast or ovarian cancer. The allele specific oligonucleotides hybridize with a target polynucleotide sequence containing the IVS6-2delA mutation. 5'TAT TTT ACA GAT GCA AA 3', SEQ ID NO:3, hybridizes preferentially to the wild type sequence and is useful as a control sequence. 5'TAT TTT ACG ATG CAA AC 31', SEQ ID NO:4, is designed to hybridize preferentially to the mutant sequence.

In a second embodiment of the invention a pair of isolated oligonucleotide primers are provided.

BRCA1-11F 5'CCA AGG TGT ATG AAG TAT GT 3', SEQ ID NO:5

BRCA1-11R 5'GTT ATG TTG GCT CCT TGC T 3', SEQ ID NO:6

The oligonucleotide primers are useful in directing amplification of a target polynucleotide prior to sequencing. These unique BRCA1 exon 11 oligonucleotide primers were used to scan the BRCA1 gene to find the mutation. From the sequence information, the probes were designed and produced for the mutation based upon identification of the the 815delTG mutation.

In another embodiment of the invention a pair of isolated allele specific oligonucleotides are provided.

5'GAC GGA TGT AAC AAA TA 3', SEQ ID NO:7

5'GAG ACG GAT AAC AAA TA 3', SEQ ID NO:8

These allele specific oligonucleotides are useful in diagnosis of a subject at risk of having breast or ovarian cancer. The allele specific oligonucleotides hybridize with a target polynucleotide sequence containing the 815delTG mutation. 5'GAC GGA TGT AAC AAA TA 3', SEQ ID NO:7, hybridizes preferentially to the wild type sequence and is useful as a control sequence. 5'GAG ACG GAT AAC AAA TA 3', SEQ ID NO:8, is designed to hybridize preferentially to the mutant sequence.

In a third embodiment of the invention a pair of isolated oligonucleotide primers are provided.

BRCA1-11F 5'CCA AGG TGT ATG AAG TAT GT 3', SEQ ID NO:5

BRCA1-11R 5'GTT ATG TTG GCT CCT TGC T 3', SEQ ID NO:6

The oligonucleotide primers are useful in directing amplification of a target polynucleotide prior to sequencing. These unique BRCA1 exon 11 oligonucleotide primers were used to scan the BRCA1 gene to find the mutation. From the sequence information, the probes were designed and produced for the mutation based upon identification of the 926ins10 mutation.

In another embodiment of the invention a pair of isolated allele specific oligonucleotides are provided.

5'CAT GTG GAG CCA TGT GGC ACA AAT ACT 3', SEQ ID NO:9

5'CAT GTG GAG CCA TGT GGA GCC ATG TGG 3', SEQ ID NO:10

These allele specific oligonucleotides are useful in diagnosis of a subject at risk of having breast or ovarian cancer. The allele specific oligonucleotides hybridize with a target polynucleotide sequence containing the 926ins10 mutation. 5'CAT GTG GAG CCA TGT GGC ACA AAT ACT 3', SEQ ID NO:9, hybridizes preferentially to the wild type sequence and is useful as a control sequence. 5'CAT GTG GAG CCA TGT GGA GCC ATG TGG 3', SEQ ID NO:10, is designed to hybridize preferentially to the mutant sequence.

In a fourth embodiment of the invention a pair of isolated oligonucleotide primers are provided.

BRCA1-11F 5'ACT GTT AGG TTC TGA TGA CT 3', SEQ ID NO:11

BRCA1-11R 5'ATC ATT TCA GGA GTC TTT TG 3', SEQ ID NO:12

The oligonucleotide primers are useful in directing amplification of a target polynucleotide prior to sequencing. These unique BRCA1 exon 11 oligonucleotide primers were used to scan the BRCA1 gene to find the mutation. From the sequence information, the probes were designed and produced for the mutation based upon identification of the 1506delA mutation.

In another embodiment of the invention a pair of isolated allele specific oligonucleotides are provided.

5'TAT TTG GGA AAA CCT AT 3', SEQ ID NO:13

5'TAT TTG GGA AAC CTA TC 3', SEQ ID NO:14

These allele specific oligonucleotides are useful in diagnosis of a subject at risk of having breast or ovarian cancer. The allele specific oligonucleotides hybridize with a target polynucleotide sequence containing the 1506delA mutation. 5'TAT TTG GGA AAA CCT AT 3', SEQ ID NO:13, hybridizes preferentially to the wild type sequence and is useful as a control sequence. 5'TAT TTG GGA AAC CTA TC 3', SEQ ID NO:14, is designed to hybridize preferentially to the mutant sequence.

In a fifth embodiment of the invention a pair of isolated oligonucleotide primers are provided.

BRCA1 -111F 5'GTA TAA GCA ATA TGG AAC TCG A 3', SEQ ID NO:15

BRCA1-11R 5'TTA AGT TCA CTG GTA TTT GAA CA 3', SEQ ID NO:16

The oligonucleotide primers are useful in directing amplification of a target polynucleotide prior to sequencing. These unique BRCA1 exon 11 oligonucleotide primers were used to scan the BRCA1 gene to find the mutation. From the sequence information, the probes were designed and produced for the mutation based upon identification of the T2034C mutation.

In another embodiment of the invention a pair of isolated allele specific oligonucleotides are provided.

5'GTA CTG AAT TGC AAA TT 3', SEQ ID NO:17

5'GTA CTG AAC TGC AAA TT 3', SEQ ID NO:18

These allele specific oligonucleotides are useful in diagnosis of a subject at risk of having breast or ovarian cancer. The allele specific oligonucleotides hybridize with a target polynucleotide sequence containing the T2034C mutation. 5'GTA CTG AAT TGC AAA TT 3', SEQ ID NO:17, hybridizes preferentially to the wild type sequence and is useful as a control sequence. 5'GTA CTG AAC TGC AAA TT 3', SEQ ID NO:18, is designed to hybridize preferentially to the mutant sequence.

In a sixth embodiment of the invention a pair of isolated oligonucleotide primers are provided.

BRCA1 -11F 5'GTA TAA GCA ATA TGG AAC TCG A 3', SEQ ID NO:15

BRCA1 -11R 5'TGG AAC AAC CAT GAA TTA GTC 3', SEQ ID NO:19

The oligonucleotide primers are useful in directing amplification of a target polynucleotide prior to sequencing. These unique BRCA1 exon 11 oligonucleotide primers were used to scan the BRCA1 gene to find the mutation. From the sequence information, the probes were designed and produced for the mutation based upon identification of the C2428A mutation.

In another embodiment of the invention a pair of isolated allele specific oligonucleotides are provided.

5'CAG TAT TTC ATT GGT AC 3', SEQ ID NO:20
5'CAG TAT TTA ATT GGT AC 3', SEQ ID NO:21

These allele specific oligonucleotides are useful in diagnosis of a subject at risk of having breast or ovarian cancer. The allele specific oligonucleotides hybridize with a target polynucleotide sequence containing the C2428A mutation. 5'CAG TAT TTC ATT GGT AC 3', SEQ ID NO:20, hybridizes preferentially to the wild type sequence and is useful as a control sequence. 5'CAG TAT TTA ATT GGT AC 3', SEQ ID NO:21, is designed to hybridize preferentially to the mutant sequence.

In a seventh embodiment of the invention a pair of isolated oligonucleotide primers are provided.

BRCA1-15F 5'TGG CTG CCC AGG AAG TAT G 3', SEQ ID NO:22

BRCA1 -15R 5'AAC CAG AAT ATC TTT ATG TAG GA 3', SEQ ID NO:23

The oligonucleotide primers are useful in directing amplification of a target polynucleotide prior to sequencing. These unique BRCA1 exon 15 oligonucleotide primers were used to scan the BRCA1 gene to find the mutation. From the sequence information, the probes were designed and produced for the mutation based upon identification of the G4643A mutation.

In another embodiment of the invention a pair of isolated allele specific oligonucleotides are provided.

5'GAT AGG TGG TAC ATG CA 3', SEQ ID NO:24
5'GAT AGG TGA TAC ATG CA 3', SEQ ID NO:25

These allele specific oligonucleotides are useful in diagnosis of a subject at risk of having breast or ovarian cancer. The allele specific oligonucleotides hybridize with a target polynucleotide sequence containing the G4643A mutation. 5'GAT AGG TGG TAC ATG CA 3', SEQ ID NO:24, hybridizes preferentially to the wild type sequence and is useful as a control sequence. 5'GAT AGG TGA TAC ATG CA 3', SEQ ID NO:25, is designed to hybridize preferentially to the mutant sequence.

In a eighth embodiment of the invention a pair of isolated oligonucleotide primers are provided.

BRCA1-16F 5'AAT TCT TAA CAG AGA CCA GAA C 3', SEQ ID NO:26

BRCA1 -16R 5'AAA ACT CTT TCC AGA ATG TTG T 3', SEQ ID NO:27

The oligonucleotide primers are useful in directing amplification of a target polynucleotide prior to sequencing. These unique BRCA1 exon 16 oligonucleotide primers were used to scan the BRCA1 gene to find the mutation. From the sequence information, the probes were designed and produced for the mutation based upon identification of the 5053delG, mutation.

In another embodiment of the invention a pair of isolated allele specific oligonucleotides are provided.

5'ACA GAA AGG GTC AAC AA 3', SEQ ID NO:28
5'ACA GAA AGG TCA ACA AA 3', SEQ ID NO:29

These allele specific oligonucleotides are useful in diagnosis of a subject at risk of having breast or ovarian cancer. The allele specific oligonucleotides hybridize with a target polynucleotide sequence containing the 5053delG mutation. 5'ACA GAA AGG GTC AAC AA 3', SEQ ID NO:28, hybridizes preferentially to the wild type sequence and is useful as a control sequence. 5'ACA GAA AGG TCA ACA AA 3', SEQ ID NO:29, is designed to hybridize preferentially to the mutant sequence.

In a ninth embodiment of the invention a pair of isolated oligonucleotide primers are provided.

BRCA1 -18F 5'GGC TCT TTA GCT TCT TAG GAC 3', SEQ ID NO:30

BRCA1 -18R 5'GAG ACC ATT TTC CCA GCA TC 3', SEQ ID NO:31

The oligonucleotide primers are useful in directing amplification of a target polynucleotide prior to sequencing. These unique BRCA1 exon 18 oligonucleotide primers were used to scan the BRCA1 gene to find the mutation. From the sequence information, the probes were designed and produced for the mutation based upon identification of the 5210delT mutation.

In another embodiment of the invention a pair of isolated allele specific oligonucleotides are provided.

5'GTT TGT GTG TGA ACG GA 3', SEQ ID NO:32
5'GTT TGT GTG GAA CGG AC 3', SEQ ID NO:33

These allele specific oligonucleotides are useful in diagnosis of a subject at risk of having breast or ovarian cancer. The allele specific oligonucleotides hybridize with a target polynucleotide sequence containing the 5210delT mutation. 5'GTT TGT GTG TGA ACG GA 3', SEQ ID NO:32, hybridizes preferentially to the wild type sequence and is useful as a control sequence. 5'GTT TGT GTG GAA CGG AC 3', SEQ ID NO:33, is designed to hybridize preferentially to the mutant sequence.

In a tenth embodiment of the invention a pair of isolated oligonucleotide primers are provided.

BRCA1 -IVS20F 5'ATA TGA CGT GTC TGC TCC AC 3', SEQ ID NO:34

BRCA1-IVS20R 5'GGG AAT CCA AAT TAC ACA GC 3', SEQ ID NO:35

The oligonucleotide primers are useful in directing amplification of a target polynucleotide prior to sequencing. These unique BRCA1 intron 20 oligonucleotide primers were used to scan the BRCA1 gene to find the mutation. It should be noted that this type of insertion mutation inserts a repeat from the adjacent naturally occurring (wild type) sequence. From the sequence information, the probes were designed and produced for the mutation based upon identification of the IVS20+40ins12 mutation.

In another embodiment of the invention a pair of isolated allele specific oligonucleotides are provided.

5'CCA CTC TGT ATT CCA CTC CCC TTT GCA G 3', SEQ ID NO:36
5'CCA CTC TGT ATT CCA CTC TGT ATT CCA C 3', SEQ ID NO:37

These allele specific oligonucleotides are useful in diagnosis of a subject at risk of having breast or ovarian cancer. The allele specific oligonucleotides hybridize with a target polynucleotide sequence containing the IVS20+40ins12 mutation. 5'CCA CTC TGT ATT CCA CTC CCC TTT GCA G 3', SEQ ID NO:36, hybridizes preferentially to the wild type sequence and is useful as a control sequence. 5'CCA CTC TGT ATT CCA CTC TGT ATT CCA C 3', SEQ ID NO:37, is designed to hybridize preferentially to the mutant sequence.

In an eleventh embodiment of the invention a pair of isolated oligonucleotide primers are provided.
BRCA1-17F 5'GTG TAG AAC GTG CAG GAT TG 3', SEQ ID NO:38
BRCA1-17R 5'TCG CCT CAT GTG GTT TTA 3', SEQ ID NO:39
The oligonucleotide primers are useful in directing amplification of a target polynucleotide prior to sequencing. These unique BRCA1 exon 17 oligonucleotide primers were used to scan the BRCA1 gene to find the mutation. From the sequence information, the probes were designed and produced for the mutation based upon identification of the 5150delT mutation.

In another embodiment of the invention a pair of isolated allele specific oligonucleotides are provided.
  5'CAC TTT AAC TAA TCT AA 3', SEQ ID NO:40
  5'CAC TTT AAC AAT CTA AT 3', SEQ ID NO:41
These allele specific oligonucleotides are useful in diagnosis of a subject at risk of having breast or ovarian cancer. The allele specific oligonucleotides hybridize with a target polynucleotide sequence containing the 5150delT mutation. 5'CAC TTT AAC TAA TCT AA 3', SEQ ID NO:40 hybridizes preferentially to the wild type sequence and is useful as a control sequence. 5'CAC TTT AAC AAT CTA AT 3', SEQ ID NO:41 is designed to hybridize preferentially to the mutant sequence.

In a twelfth embodiment of the invention a pair of isolated oligonucleotide primers are provided.
BRCA1-l11F 5'GAA GTA ATT GTA AGC ATC CT 3'SEQ ID NO:42
BRCA1-11R 5'CAT TTT GTT TCC TCA CTA AG 3'SEQ ID NO:43
The oligonucleotide primers are useful in directing amplification of a target polynucleotide prior to sequencing. These unique BRCA1 exon 11 oligonucleotide primers were used to scan the BRCA1 gene to find the mutation. From the sequence information, the probes were designed and produced for the mutation based upon identification of the C3904A mutation.

In another embodiment of the invention a pair of isolated allele specific oligonucleotides are provided.
  5'TTA TTA TCA TTG AAG AA 3', SEQ ID NO:44
  5'TTA TTA TAA TTG AAG AA 3', SEQ ID NO:45
These allele specific oligonucleotides are useful in diagnosis of a subject at risk of having breast or ovarian cancer. The allele specific oligonucleotides hybridize with a target polynucleotide sequence containing the C3904A mutation. 5'TTA TTA TCA TTG AAG AA 3', SEQ ID NO:44, hybridizes preferentially to the wild type sequence and is useful as a control sequence. 5'TTA TTA TAA TTG AAG AA 3', SEQ ID NO:45, is designed to hybridize preferentially to the mutant sequence.

In a thirteenth embodiment of the invention a pair of isolated oligonucleotide primers are provided.
BRCA1 -l11F 5'GCA AAA GCG TCC AGA AAG AG 3', SEQ ID NO:46
BRCA1-11R 5'AGT CTT CCA ATT CAC TGC AC 3', SEQ ID NO:47

The oligonucleotide primers are useful in directing amplification of a target polynucleotide prior to sequencing. These unique BRCA1 exon 11 oligonucleotide primers were used to scan the BRCA1 gene to find the mutation. From the sequence information, the probes were designed and produced for the mutation based upon identification of the 3888delGA mutation.

In another embodiment of the invention a pair of isolated allele specific oligonucleotides are provided.
  5'GAA CAC AGG AGA AT 3', SEQ ID NO:48
  5'TAA GAA CAC AGG AG 3', SEQ ID NO:49
These allele specific oligonucleotides are useful in diagnosis of a subject at risk of having breast or ovarian cancer. The allele specific oligonucleotides hybridize with a target polynucleotide sequence containing the 3888delGA mutation. 5'GAA CAC AGG AGA AT 3', SEQ ID NO:48, hybridizes preferentially to the wild type sequence and is useful as a control sequence. 5'TAA GAA CAC AGG AG 3', SEQ ID NO:49, is designed to hybridize preferentially to the mutant sequence.

In a fourteenth embodiment of the invention a pair of isolated oligonucleotide primers are provided.
BRCA1 -11F 5'CCA AGG TGT ATG AAG TAT GT 3', SEQ ID NO:5
BRCA1 -11R 5'GTT ATG TTG GCT CCT TGC T 3', SEQ ID NO:6
The oligonucleotide primers are useful in directing amplification of a target polynucleotide prior to sequencing. These unique BRCA1 exon 11 oligonucleotide primers were used to scan the BRCA1 gene to find the mutation. From the sequence information, the probes were designed and produced for the mutation based upon identification of the T903G mutation.

In another embodiment of the invention a pair of isolated allele specific oligonucleotides are provided.
  5'GAA AAG TAT CAG GGT AG 3', SEQ ID NO:50
  5'GAA AAG TAG CAG GGT AG 3', SEQ ID NO:51
These allele specific oligonucleotides are useful in diagnosis of a subject at risk of having breast or ovarian cancer. The allele specific oligonucleotides hybridize with a target polynucleotide sequence containing the T903G mutation. 5'GAA AAG TAT CAG GGT AG 3', SEQ ID NO:50, hybridizes preferentially to the wild type sequence and is useful as a control sequence. 5'GAA AAG TAG CAG GGT AG 3', SEQ ID NO:51, is designed to hybridize preferentially to the mutant sequence.

In a fifteenth embodiment of the invention a pair of isolated oligonucleotide primers are provided.
BRCA1 -11F 5'CTA AGA ACA CAG AGG AGA A 3', SEQ ID NO:52
BRCA1-11R 5'CTA GCT GTG TGA AGG ACT 3', SEQ ID NO:53
The oligonucleotide primers are useful in directing amplification of a target polynucleotide prior to sequencing. These unique BRCA1 exon 11 oligonucleotide primers were used to scan the BRCA1 gene to find the mutation. From the sequence information, the probes were designed and produced for the mutation based upon identification of the A4164C mutation.

In another embodiment of the invention a pair of isolated allele specific oligonucleotides are provided.
  5'AAG AGG AAC GGG CTT GG 3', SEQ ID NO:54
  5'AAG AGG ACC GGG CTT GG 3', SEQ ID NO:55
These allele specific oligonucleotides are useful in diagnosis of a subject at risk of having breast or ovarian cancer. The allele specific oligonucleotides hybridize with a target polynucleotide sequence containing the A4164C mutation. 5'AAG AGG AAC GGG CTT GG 3', SEQ ID NO:54, hybridizes preferentially to the wild type sequence and is useful as a control sequence. 5'AAG AGG ACC GGG CTT GG 3', SEQ ID NO:55, is designed to hybridize preferentially to the mutant sequence.

The primers of the invention embrace oligonucleotides of sufficient length and appropriate sequence so as to provide initiation of polymerization on a significant number of nucleic acids in the polymorphic locus. Preferred sequences for the present invention are:

5'CAC AAC AAA GAG CAT ACA TAG GG 3', SEQ ID NO:1,
5'TCG GGT TCA CTC TGT AGA AG 3', SEQ ID NO:2,
5'CCA AGG TGT ATG AAG TAT GT 3', SEQ ID NO:5,
5'GTT ATG TTG GCT CCT TGC T 3', SEQ ID NO:6,
5'ACT GTT AGG TTC TGA TGA CT 3', SEQ ID NO:11,
5'ATC ATT TCA GGA GTC TTT TG 3', SEQ ID NO:12,
5'GTA TAA GCA ATA TGG AAC TCG A 3', SEQ ID NO:15,
5'TTA AGT TCA CTG GTA TTT GAA CA 3', SEQ ID NO:16,
5'TGG AAC AAC CAT GAA TTA GTC 3', SEQ ID NO:19,
5'TGG CTG CCC AGG AAG TAT G 3', SEQ ID NO:22,
5'AAC CAG AAT ATC TTT ATG TAG GA 3', SEQ ID NO:23,
5'AAT TCT TAA CAG AGA CCA GAA C 3', SEQ ID NO:26,
5'AAA ACT CTT TCC AGA ATG TTG T 3', SEQ ID NO:27,
5'GGC TCT TTA GCT TCT TAG GAC 3', SEQ ID NO:30,
5'GAG ACC ATT TTC CCA GCA TC 3', SEQ ID NO:31,
5'ATA TGA CGT GTC TGC TCC AC 3', SEQ ID NO:34,
5'GGG AAT CCA AAT TAC ACA GC 3', SEQ ID NO:35,
5'GTG TAG AAC GTG CAG GAT TG 3', SEQ ID NO:38,
5'TCG CCT CAT GTG GTT TTA 3', SEQ ID NO:39,
5'GAA GTA ATT GTA AGC ATC CT 3', SEQ ID NO:42,
5'CAT TTT GTT TCC TCA CTA AG 3', SEQ ID NO:43,
5'GCA AAA GCG TCC AGA AAG AG 3', SEQ ID NO:46,
5'AGT CTT CCA ATT CAC TGC AC 3', SEQ ID NO:47,
5'CTA AGA ACA CAG AGG AGA A 3', SEQ ID NO:52, and
5'CTA GCT GTG TGA AGG ACT 3', SEQ ID NO:53.

Environmental conditions conducive to synthesis of extension products include the presence of nucleoside triphosphates, an agent for polymerization, such as DNA polymerase, and suitable conditions such as temperature, ionic strength and pH. The primer is preferably single stranded for maximum efficiency in amplification, but may be double stranded. If double stranded, the primer is first treated to separate its strands before being used to prepare extension products. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it may contain fewer nucleotides.

Primers of the invention are designed to be "substantially" complementary to each strand of the genomic locus to be amplified. This means that the primers must be sufficiently complementary to hybridize with their respective strands under conditions which allow the agent for polymerization to perform. In other words, the primers should have sufficient complementarity with the 5'and 3'sequences flanking the mutation to hybridize therewith and permit amplification of the genomic locus. "Substantially" the same as it refers to oligonucleotide sequences also refers to the functional ability to hybridize or anneal with sufficient specificity to distinguish between the presence or absence of the mutation. This is measurable by the temperature of melting being sufficiently different to permit easy identification of whether the oligonucleotide is binding to the normal or mutant BRCA1 gene sequence. oligonucleotide primers of the invention are employed in the amplification process which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA polymerase I (Klenow) and nucleotides, results in newly synthesized + and − strands containing the target polymorphic locus sequence. Because these newly synthesized sequences are also templates, repeated cycles of denaturing, primer annealing, and extension results in exponential production of the region (i.e., the target polymorphic locus sequence) defined by the primers. The product of the chain reaction is a discreet nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al., *Tetrahedron Letters*, 22:1859–1862, (1981). One method for synthesizing oligonucleotides on a modified solid support is described in U.S. Pat. No. 4,458,066.

Any nucleic acid specimen, in purified or nonpurified form, can be utilized as the starting nucleic acid or acids, providing it contains, or is suspected of containing, the specific nucleic acid sequence containing the polymorphic locus. Thus, the process may amplify, for example, DNA or RNA, including messenger RNA, wherein DNA or RNA may be single stranded or double stranded. In the event that RNA is to be used as a template, enzymes, and/or conditions optimal for reverse transcribing the template to CDNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the polymorphic locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

DNA utilized herein may be extracted from a body sample, such as blood, tissue material and the like by a variety of techniques such as that described by Maniatis, et. al. in *Molecular Cloning:A Laboratory Manual*, Cold Spring Harbor, N.Y., p 280–281, 1982). If the extracted sample is impure, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates DATP, dCTP, dGTP, and dTTP are added to the synthesis mixture, either separately or together with the primers, in adequate amounts and the resulting solution is heated to about 90°–100° C.

from about 1 to 10 minutes, preferably from 1 to 4 minutes. This is sufficient to denature any double strands. After this heating period, the solution is allowed to cool at a rate which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Thermostable DNA polymerases, such as Taq polymerase may function at a higher temperature.

The agent for polymerization may be any compound or system which will function to accomplish the synthesis of primer extension products, including enzymes. Suitable enzymes for this purpose include, for example, $E.\ coli$ DNA polymerase I, Klenow fragment of $E.\ coli$ DNA polymerase, polymerase muteins, reverse transcriptase, other enzymes, including heat-stable enzymes (i.e., those enzymes which perform primer extension after being subjected to temperatures sufficiently elevated to cause denaturation), such as Taq polymerase. The suitable enzyme will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths.

The newly synthesized strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The steps of denaturing, annealing, and extension product synthesis can be repeated as often as needed to amplify the target polymorphic locus nucleic acid sequence to the extent necessary for detection. The amount of the specific nucleic acid sequence produced will accumulate in an exponential fashion. PCR. A Practical Approach, ILR Press, Eds. M. J. McPherson, P. Quirke, and G. R. Taylor, 1992.

The amplification products may be detected by analyzing it by Southern blots without using radioactive probes. In such a process, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation. In the preferred embodiment, the amplification products are determinable by separating the mixture on an agarose gel containing ethidium bromide which causes DNA to be fluorescent.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et.al., $Bio/Technology$, 3:1008–1012, (1985)), allele-specific oligonucleotide (ASO) probe analysis (Conner, et. al., $Proc.\ Natl.\ Acad.\ Sci.\ U.S.A.$, 80:278, (1983)), oligonucleotide ligation assays (OLAs) (Landgren, et. al., $Science$, 241:1007, (1988)), and the like. Molecular techniques for DNA analysis have been reviewed (Landgren, et. al., $Science$, 242:229–237, (1988)).

Preferably, the method of amplifying is by PCR, as described herein and as is commonly used by those of ordinary skill in the art. Alternative methods of amplification have been described and can also be employed as long as the BRCA1 locus amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA. Another nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is $10^8$ to $10^9$ fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligonucleotide probe pairs, and the RCR fills and joins the gap, mimicking normal DNA repair. Nucleic acid amplification by strand displacement activation (SDA) utilizes a short primer containing a recognition site for Hinc II with short overhang on the 5' end which binds to target DNA. A DNA polymerase fills in the part of the primer opposite the overhang with sulfur-containing adenine analogs. Hinc II is added but only cuts the unmodified DNA strand. A DNA polymerase that lacks 5' exonuclease activity enters at the cite of the nick and begins to polymerize, displacing the initial primer strand downstream and building a new one which serves as more primer. SDA produces greater than $10^7$-fold amplification in 2 hours at 37° C. Unlike PCR and LCR, SDA does not require instrumented Temperature cycling. Another amplification system useful in the method of the invention is the QB Replicase System. Although PCR is the preferred method of amplification in the invention, these other methods can also be used to amplify the BRCA1 locus as described in the method of the invention.

In another embodiment of the invention, a method is provided for diagnosing a subject having a predisposition or higher susceptibility to (at risk of) breast or ovarian cancer comprising sequencing a target nucleic acid of a sample from a subject by dideoxy sequencing following amplification of the target nucleic acid. In such an embodiment, one does not even need to use any of the oligonucleotides, either primers or probes as described herein. The BRCA1 gene, or fragments thereof, may be directly cloned and then sequenced (such as by dideoxy methods) to determine the presence of absence of a mutation. In such a situation, one need only compare the sequence obtained to a naturally occurring (wild type) BRCA1 gene, or portion thereof.

Other methods of DNA sequencing such as those of Sanger et al, *Proc. Natl. Acad. Sci. USA*, 74: 5463 (1977) or Maxam et al, *Proc. Natl. Acad. Sci. USA*, 74: 560 (1977) or other methods known in the art may be used.

In another embodiment of the invention a method is provided for diagnosing a subject having a predisposition or higher susceptibility to (at risk of) breast or ovarian cancer comprising contacting a target nucleic acid of a sample from a subject with a reagent that detects the presence of one of the mutations of the present invention and detecting the mutation.

In another embodiment of the invention, a method and reagents are provided for repairing the gene mutation in at least some cells by applying an oligomer comprising the sequence of the wild-type probes to repair the individual's genome or gametes by triple strand hybridization. See U.S. Pat. Nos. 5,650,316 and 5,624,803 for example. This is a form of gene therapy to correct the defect in either apparently normal tissue or in an active tumor. Gene repair may also be performed on excized tumor cells which may be helpful in determining the preferred therapy to be used, particularly the reagents used for gene therapy. Other forms of gene therapy, such as providing a complete copy of a normal BRCA1 gene may also be used.

In another embodiment of the invention a method is provided for characterizing a tumor. Histologic type, morphologic grade, differences between inherited and sporadic breast cancer do not appear to be distinguished. One method comprises sequencing the target nucleic acid isolated from the tumor or other biological sample to determine if the mutation is has occurred or is present. Sanger, et al., *J. Mol. Biol.* 142:1617 (1980).

Characterizing a tumor as having originated from an inherited breast cancer gene may be clinically significant as the prevalence of bilateral breast cancer is higher than in sporadic cases. Weber, Scientific American, JANUARY-FEBRUARY p. 12–21 (1996). The tumor may be classified based on tissue taken from the tumor itself or from a non-tumor site which contains DNA.

Yet another embodiment of the present invention is an isolated mutant BRCA1 DNA sequence which may be the entire sequence, an intron, an exon thereof or a fragment or combination thereof. The DNA sequence must contain at least one mutation from the list: IVS6-2delA, 815delTG, 926ins10, 1506delA, T2034C, C2428A, G4643A, 5053delG, 5210delT, IVS20+40ins12, 5150delT, C3904A, 3888delGA, T903G or A4164C. Preferably, the isolated DNA sequence contains a sequence complementary to at least one of the following: SEQ ID NO:4, SEQ ID NO:8, SEQ ID NO:10, SEQ ID NO:14:, SEQ ID NO:18, SEQ ID NO:21, SEQ ID NO:25, SEQ ID NO:29, SEQ ID NO:33, SEQ ID NO:37, SEQ ID NO:41, SEQ ID NO:45, SEQ ID NO:49, SEQ ID NO:51 or SEQ ID NO:55. This sequence has usefulness alone, or after cloning and expression to determine suitable treatments to prevent formation of a tumor, prevent transmission of the mutant gene to offspring or to decide other prophylactic diagnostic and treatment protocols. The isolated DNA sequence may also be used for drug design by protein replacement, protein mimetics, screening known and unknown compounds, anti-idiotype antibodies to the BRCA1 active site, for the preparation of an immunogen or vaccine and determining appropriate gene therapy to counter the pathology associated with the mutant BRCA1 gene. For diagnostic purposes, knowing the mutant BRCA1 sequence for comparison purposes is the critical step in diagnosis.

Another method comprises contacting a target nucleic acid of a sample from a subject with a reagent that detects the presence of the mutation and detecting the mutation. A number of hybridization methods are well known to those skilled in the art. Many of them are useful in carrying out the invention.

The materials for use in the method of the invention are ideally suited for the preparation of a diagnostic kit. Such a kit may comprise a carrier means being compartmentalized to receive in close confinement one or more container means such as vials, tubes, and the like, each of the container means comprising one or more of the separate elements to be used in the method. For example, one of the container means may comprise means for amplifying BRCA1 DNA, said means comprising the necessary enzyme(s) and oligonucleotide primers for amplifying said target DNA from the subject. Another container may contain oligonucleotide probes for detecting the presence or absence of a mutation.

The oligonucleotide primers include primers having a sequence of SEQ ID NO's: 1, 2, 5, 6, 11, 12, 15, 16, 19, 22, 23, 26, 27, 30, 31, 34, 35, 37, 38, 42, 43, 46, 47, 52 or 53 or primer sequences substantially complementary or substantially homologous thereto. Other primers flanking the BRCA1 locus or a region containing one of the mutation sites may be used. The target flanking 5' and 3' polynucleotide sequence include other oligonucleotide primers for amplifying the BRCA1 locus will be known or readily ascertainable to those of skill in the art.

Oligonucleotide probes including probes having substantially the sequence of SEQ ID NO's 3, 4, 7, 8, 9, 10, 13, 14, 17, 18, 20, 21, 24, 25, 28, 29, 32, 33, 36, 37, 40, 41, 44, 45, 48, 49, 50, 51, 54, and 55. Other oligonucleotide probes which hybridize to one or more of the BRCA1 mutation sites and sequences substantially complementary or homologous thereto may be used. Other oligonucleotide probes for detecting the mutations will be known or readily ascertainable to those of skill in the art.

The following definitions are provided for the purpose of understanding this invention.

The term "primer" as used herein refers to a sequence comprising two or more deoxyribonucleotides or ribonucleotides, preferably more than three, and more preferably more than eight and most preferably at least 20 nucleotides of the BRCA1 gene wherein the sequence corresponds to a sequence flanking one of the mutations or wild type sequences of BRCA1 corresponding to the mutation sites. Primers may be used to initiate DNA synthesis via the PCR. Oligonucleotides of the present invention can be used for primer hybridization and others will be known or readily ascertainable to those of skill in the art. The primers of the present invention include the sequences recited and complementary sequences which would anneal to the opposite DNA strand of the sample target. Since both strands of DNA are complementary and mirror images of each other, the same segment of DNA will be amplified.

The term "substantially complementary to" or "substantially the sequence" refers to sequences which hybridize to the sequences provided under stringent conditions and/or sequences having sufficient homology with, (e.g. SEQ ID NO:3 and SEQ ID NO:4) such that the allele specific oligonucleotides of the invention hybridize to the sequence.

"Isolated" as used herein refers to being substantially free of other polynucleic acids, proteins, lipids, carbohydrates or other materials with which they may be associated. Such association is typically either in cellular material or in a synthesis medium.

"Biological sample" referrs to a polynucleotide containing sample originally from a biological source. The sample may be from a living, dead or even archeological source from a variety of tissues and cells. Examples include: body fluid [blood (leukocytes), urine (epithelial cells), saliva, cervical and vaginal secretions . . . ] skin, hair roots/folicle, mucus membrane (e.g. buccal or tongue cell scrapings), cervicovaginal cells (from PAP smear, etc.) internal tissue (normal or tumor), chorionic villus tissue, amnionic cells, placental cells, fetal cells, cord blood, sperm or egg.

"Coding sequence" or "DNA coding sequence" refers to those portions of a gene which, taken together, code for a peptide (protein), or for which the nucleic acid itself has function.

A "target polynucleotide" refers to the nucleic acid sequence of interest e.g., the BRCA1 encoding polynucleotide.

"Consensus" means the most commonly occurring in the population.

"Substantially complementary to" refers to probe or primer sequences which hybridize to the sequences provided under stringent conditions and/or sequences having sufficient homology with test polynucleotide sequences, such that the allele specific oligonucleotide probe or primers hybridize to the test polynucleotide sequences to which they are complimentary.

"Sequence variation" as used herein refers to any difference in nucleotide sequence between two different oligonucleotide or polynucleotide sequences.

"Polymorphism" as used herein refers to a sequence variation in a gene which is not necessarily associated with pathology.

"Mutation" as used herein refers to an altered genetic sequence which results in the gene coding for a non-functioning protein or a protein with substantially reduced or altered function. Generally, a deleterious mutation is associated with pathology or the potential for pathology.

"Predetermined sequence variation" as used herein refers to a nucleotide sequence that is designed to be different than the corresponding sequence in a reference nucleotide sequence. A predetermined sequence variation can be a known mutation in a BRCA1 gene.

"BRCA1 gene" is a group of compounds and refers to the gene sequences, those appearing in the GENBANK database and those in the BIC database. Other different sequences include polymorphisms and genetic alterations, especially those which define other haplotypes for the BRCA1 gene. Generally polymorphisms which don't cause an amino acid change or which are naturally occurring (wild types), which are not associated with pathology are also considered the BRCA1 gene. For Example, see U.S. Pat. No. 5,654,155 and Shattuck-Eidens, et al., *Journal of the American Medical Association*, 287: 1242–1250 (1997). The corresponding nucleotides would then be used even if the nucleotide number differs. Generally, the sense strand is referred to. While the BRCA1 gene discussed herein is the human BRCA1 gene, the corresponding assays and reagents for the gene in other animals may also be used. The BRCA1 gene includes the coding sequences, non-coding sequences (e.g. introns) and regulatory regions affecting gene expression.

"Allele specific detection assay" as used herein refers to an assay to detect the presence or absence of a predetermined sequence variation in a test polynucleotide or oligonucleotide by annealing the test polynucleotide or oligonucleotide with a polynucleotide or oligonucleotide of predetermined sequence such that differential DNA sequence based techniques or DNA amplification methods discriminate between normal and mutant.

"Sequence variation locating assay" as used herein refers to an assay that detects a sequence variation in a test polynucleotide or oligonucleotide and localizes the position of the sequence variation to a sub-region of the test polynucleotide, without necessarily determining the precise base change or position of the sequence variation.

"Region" as used herein generally refers to an area from several nucleotides upstream to several nucleotides downstream from the specific nucleotide mentioned. "Region" also includes the complementary nucleotides on the antisense strand of sample DNA.

"Targeted confirmatory sequencing" as used herein refers to sequencing a polynucleotide in the region wherein a sequence variation has been located by a sequence variation locating assay in order to determine the precise base change and/or position of the sequence variation.

"Probe" includes any oligonucleotide which hybridizes to a BRCA1 or mutant BRCA1 sequence. The probe may be labled (directly or indirectly) or it may act as a primer such as a PCR primer. The probes of the present invention include the sequences recited and complementary sequences which would anneal to the antisense strand of the sample target DNA. Since both strands of DNA are complementary and mirror immages of each other, the complementary version of the mutation is equally unique and indicative of the mutation to be assayed.

Allele Specific Oligonucleotide hybridization is sometimes referred to ASO or the ASO method.

The invention in several of its embodiments includes:

DETECTION OF PREDETERMINED SEQUENCE VARIATIONS

Stage I analysis is used to determine the presence or absence of a predetermined nucleotide sequence variation; preferably a known mutation or set of known mutations in the test gene. In accordance with the invention, such predetermined sequence variations are detected by allele specific hybridization, a sequence-dependent-based technique which permits discrimination between normal and mutant alleles. An allele specific assay is dependent on the differential ability of mismatched nucleotide sequences (e.g., normal:mutant) to hybridize with each other, as compared with matching (e.g., normal:normal or mutant:mutant) sequences.

DETECTION OF PREDETERMINED SEQUENCE VARIATIONS USING ALLELE SPECIFIC HYBRIDIZATION

A variety of methods well-known in the art can be used for detection of predetermined sequence variations by allele specific hybridization. Preferably, the test gene is probed with allele specific oligonucleotides (ASOs); and each ASO contains the sequence of a known mutation. ASO analysis detects specific sequence variations in a target polynucleotide fragment by testing the ability of a specific oligonucleotide probe to hybridize to the target polynucleotide fragment. Preferably, the oligonucleotide contains the mutant sequence (or its complement). The presence of a sequence variation in the target sequence is indicated by hybridization between the oligonucleotide probe and the target fragment under conditions in which an oligonucleotide probe containing a normal sequence does not hybridize to the target fragment. A lack of hybridization between the sequence variant (e.g., mutant) oligonucleotide probe and the target polynucleotide fragment indicates the absence of the specific sequence variation (e.g., mutation) in the target fragment. In a preferred embodiment, the test samples are probed in a standard dot blot format. Each region within the test gene that contains the sequence corresponding to the ASO is individually applied to a solid surface, for example, as an individual dot on a membrane. Each individual region can be produced, for example, as a separate PCR amplification product using methods well-known in the art (see, for example, the experimental embodiment set forth in Mullis, K. B., 1987, U.S. Pat. No. 4,683,202). The use of such a dot blot format is described in detail in the Examples below, detailing the Stage I analysis of the human BRCA1 gene to detect the presence or absence of several different known mutations using several corresponding ASOs.

Membrane-based formats that can be used as alternatives to the dot blot format for performing ASO analysis include, but are not limited to, reverse dot blot, (multiplex amplification assay), and multiplex allele-specific diagnostic assay (MASDA).

In a reverse dot blot format, oligonucleotide or polynucleotide probes having known sequence are immobilized on the solid surface, and are subsequently hybridized with the labeled test polynucleotide sample. In this situation, the primers may be labeled or the NTPs maybe labeled prior to amplification to prepare a labeled test polynucleotide sample. Alternatively, the test polynucleotide sample may be labeled subsequent to isolation and/or synthesis In a multiplex format, individual samples contain multiple target sequences within the test gene, instead of just a single target sequence. For example, multiple PCR products each containing at least one of the ASO target sequences are applied within the same sample dot. Multiple PCR products can be produced simultaneously in a single amplification reaction using the methods of Caskey et al., U.S. Pat. No. 5,582,989. The same blot, therefore, can be probed by each ASO whose corresponding sequence is represented in the sample dots.

A MASDA format expands the level of complexity of the multiplex format by using multiple ASOs to probe each blot (containing dots with multiple target sequences). This procedure is described in detail in U.S. Pat. No. 5,589,330 by A. P. Shuber, and in Michalowsky et al., *American Journal of Human Genetics*, 59(4): A272, poster 1573 (October 1996), each of which is incorporated herein by reference in its entirety. First, hybridization between the multiple ASO probe and immobilized sample is detected. This method relies on the prediction that the presence of a mutation among the multiple target sequences in a given dot is sufficiently rare that any positive hybridization signal results from a single ASO within the probe mixture hybridizing with the corresponding mutant target. The hybridizing ASO is then identified by isolating it from the site of hybridization and determining its nucleotide sequence.

Suitable materials that can be used in the dot blot, reverse dot blot, multiplex, and MASDA formats are well-known in the art and include, but are not limited to nylon and nitrocellulose membranes.

When the target sequences are produced by PCR amplification, the starting material can be chromosomal DNA in which case the DNA is directly amplified. Alternatively, the starting material can be mRNA, in which case the mRNA is first reversed transcribed into cDNA and then amplified according to the well known technique of RT-PCR (see, for example, U.S. Pat. No. 5,561,058 by Gelfand et al.).

The methods described above are suitable for moderate screening of a limited number of sequence variations. However, with the need in molecular diagnosis for rapid, cost effective large scale screening, technologies have developed that integrate the basic concept of ASO, but far exceed the capacity for mutation detection and sample number. These alternative methods to the ones described above include, but are not limited to, large scale chip array sequence-based techniques. The use of large scale arrays allows for the rapid analysis of many sequence variants. A review of the differences in the application and development of chip arrays is covered by Southern, E. M., *Trends In Genetics*, 12: 110–115 (March 1996) and Cheng et al., *Molecular Diagnosis*, 1:183–200 (September 1996). Several approaches exist involving the manufacture of chip arrays. Differences include, but not restricted to: type of solid support to attach the immobilized oligonucleotides, labeling techniques for identification of variants and changes in the sequence-based techniques of the target polynucleotide to the probe.

A promising methodology for large scale analysis on 'DNA chips' is described in detail in Hacia et al., *Nature Genetics*, 14:441–447 (1996), which is hereby incorporated by reference in its entirety. As described in Hacia et al., high density arrays of over 96,000 oligonucleotides, each 20 nucleotides in length, are immobilized to a single glass or silicon chip using light directed chemical synthesis. Contingent on the number and design of the oligonucleotide probe, potentially every base in a sequence can be interrogated for alterations. Oligonucleotides applied to the chip, therefore, can contain sequence variations that are not yet known to occur in the population, or they can be limited to mutations that are known to occur in the population.

Prior to hybridization with olignucleotide probes on the chip, the test sample is isolated, amplified and labeled (e.g. fluorescent markers) by means well known to those skilled in the art. The test polynucleotide sample is then hybridized to the immobilized oligonucleotides. The intensity of sequence-based techniques of the target polynucleotide to the immobilized probe is quantitated and compared to a reference sequence. The resulting genetic information can be used in molecular diagnosis. A common, but not limiting, utility of the 'DNA chip' in molecular diagnosis is screening for known mutations. However, this may impose a limitation to the technique by only looking at mutations that have been described in the field. The present invention allows allele specific hybridization analysis be performed with a far greater number of mutations than previously available. Thus, the efficiency and comprehensiveness of large scale ASO analysis will be broadened, reducing the need for cumbersome end-to-end sequence analysis, not only with known mutations but in a comprehensive manner all mutations which might occur as predicted by the principles accepted, and the cost and time associated with these cumbersome tests will be decreased.

EXAMPLE

Genomic DNA (at least about 100 ng) is isolated from white blood cells of a subject with a family history of breast, ovarian or other cancer. Dideoxy sequence analysis is performed following polymerase chain reaction amplification of a segment of intron 6, exons 11, 15, 16, 17, 18 and intron 20.

Each segment of the BRCA1 gene is subjected to direct dideoxy sequence analysis by asymmetric amplification using the polymerase chain reaction (PCR) to generate a single stranded product amplified from this DNA sample. Shuldiner, et al., Handbook of Techniques in Endocrine Research, p. 457–486, DePablo,F., Scanes, C., eds., Academic Press, Inc., 1993. Fluorescent dye is attached for automated sequencing using the TAQ DYE TERMINATOR KIT (PERKIN-ELMER™ cat# 401628). DNA sequencing is performed in both forward and reverse directions on an APPLIED BIOSYSTEMS, INC. (ABI) automated sequencer (Model 377). The software used for analysis of the resulting data is "SEQUENCE NAVIGATOR" purchased through ABI.

The methods of the invention, which can be used to detect sequence variations in any polynucleotide sample, are demonstrated in the Example set forth in this section, for the purpose of illustration, for one gene in particular, namely, the human BRCA1 gene. The BRCA1 coding sequence is approximately 5589 base pairs and the entire gene is approximately 100,000 base pairs encoding the 1863 amino acids BRCA1 protein.

Designing an Allele Specific Oligonucleotide (ASO) Probe

An allele specific oligonucleotide probe is a short, single stranded polynucleotide that is engineered to hybridize exactly to a target sequence under a given set of conditions. Routinely, ASO probes are designed to contain sequences identical to the normal allele and sequence variation respectively. Hybridization of the probe to the target allows for the discrimination of a variant sample. Under stringent conditions, a probe with a variation as simple as a single-base pair will not hybridize to a normal sequence due to a destabilizing effect of the normal-mutant duplex (Ikuta, S. et al, Nucleic Acids Research, 15: 797–811 (1987). For use in this invention, probes were used to discriminate between a wild-type or normal sequence from one that is mutated. Each probe pair contained a polynucleotide sequence that encompassed an area that would identify a selected mutation of the BRCA 1 gene.

The design of an ASO hybridization probe must meet two basic requirements. (Current Protocols in Human Genetics, section 9.4, (1995)). First, probes that are used together in the same pool should be around the same length. Although the standard length of a probe is optimally 17 base pairs, the range can be as short as about 14 or as long as about 27. If the mutation contains a long insertion, a longer probe may be desirable. Second, the mismatched region should not be placed at the end of the 17 base pair probe, but approximately in the middle of the sequence, approximately 5–7 bases from the 5' end of the probe. In addition, the placement of a mismatch, in the case of a longer probe, should not be at the end, but at a position that allows strong hybridization and stabilization of the polynucleotide strand. In order to minimize the effects of variations in base composition of the probes, tetramethylammonium chloride is used as in the ASO hybrid's buffer (Shuber, T., U.S. Pat. No. 5,633,134). Conventionally, ASO probes are synthesized on a DNA synthesizer. They can be labeled with isotopic or non-isotopic detection agents using means familiar to those of skill in the art. The process outlined in this application for making and using probes can be applicable for other gene sequences.

DETAILED METHOD FOR THE DETECTION OF SEQUENCE VARIATIONS IN POLYNUCLEOTIDES

Isolation of Genomic DNA

White blood cells were collected from the patient and genomic DNA is extracted from the white blood cells according to well-known methods (Sambrook, et al., Molecular Cloning, A Laboratory Manual, 2nd Ed., 1989, Cold Spring Harbor Laboratory Press, at 9.16–9.19).

PCR Amplification for Sequencing

The genomic DNA is used as a template to amplify a separate DNA fragment encompassing the site of the mutation to be tested. The 25 µl PCR reaction contained the following components: 1 µl template (100 ng/µl) DNA, 2.5 µl 10× PCR Buffer (PERKIN-ELMER), 1.5 µl dNTP (2 mM each DATP, dCTP, dGTP, dTTP), 1.5 µl Forward Primer (10 µM), 1.5 µl Reverse Primer (10 µM), 0.5 µl (2.5U total) AMPLITAQ GOLD™ TAQ DNA POLYMERASE or AMPLITAQ® TAQ DNA POLYMERASE (PERKIN-ELMER), 1.0 to 5.0 µl (25 mM) MgCl$_2$ (depending on the primer) and distilled water (dH$_2$O) up to 25 µl. All reagents for each exon except the genomic DNA can be combined in a master mix and aliquoted into the reaction tubes as a pooled mixture.

For each exon analyzed, the following control PCRs were set up:

(1) "Negative" DNA control (100 ng placental DNA (SIGMA CHEMICAL CO., St. Louis, Mo.)

(2) Three "no template" controls

PCR for all exons is performed using the following thermocycling conditions:

| Temperature | Time | Number of Cycles |
|---|---|---|
| 95° C. | 5 min. (AMPLITAQ) or 10 min. (GOLD) | 1 |
| 95° C. | 30 sec. | |
| 55° C. | 30 sec. | 30 cycles |
| 72° C. | 1 min | |
| 72° C. | 5 min. | 1 |
| 4° C. | infinity | 1 |

Quality control agarose gel of PCR amplification:

The quality of the PCR products were examined prior to further analysis by electrophoresing an aliquot of each PCR reaction sample on an agarose gel. 5 µl of each PCR reaction is run on an agarose gel along side a DNA 100 BP DNA LADDER (Gibco BRL cat# 15628–019). The electrophoresed PCR products were analyzed according to the following criteria:

Each patient sample must show a single band of the size corresponding the number of base pairs expected from the length of the PCR product from the forward primer to the reverse primer. If a patient sample demonstrates smearing or multiple bands, the PCR reaction must be repeated until a clean, single band is detected. If no PCR product is visible or if only a weak band is visible, but the control reactions with placental DNA template produced a robust band, the patient sample should be re-amplified with 2× as much template DNA.

All three "no template" reactions must show no amplification products. Any PCR product present in these reactions is the result of contamination. If any one of the "no template" reactions shows contamination, all PCR products should be discarded and the entire PCR set of reactions should be repeated after the appropriate PCR decontamination procedures have been taken.

The optimum amount of PCR product on the gel should be between 50 and 100 ng, which can be determined by comparing the intensity of the patient sample PCR products with that of the DNA ladder. If the patient sample PCR products contain less than 50 to 100 ng, the PCR reaction should be repeated until sufficient quantity is obtained.

DNA Sequencing

For DNA sequencing, double stranded PCR products are labeled with four different fluorescent dyes, one specific for each nucleotide, in a cycle sequencing reaction. With Dye Terminator Chemistry, when one of these nucleotides is incorporated into the elongating sequence it causes a termination at that point. Over the course of the cycle sequencing reaction, the dye-labeled nucleotides are incorporated along the length of the PCR product generating many different length fragments.

The dye-labeled PCR products will separate according to size when electrophoresed through a polyacrylamide gel. At the lower portion of the gel on an ABI automated sequencers, the fragments pass through a region where a laser beam continuously scans across the gel. The laser excites the fluorescent dyes attached to the fragments causing the emission of light at a specific wavelength for each dye. Either a photomultiplier tube (PMT) detects the fluorescent light and converts is into an electrical signal (ABI 373) or the light is collected and separated according to wavelength by a spectrograph onto a cooled, charge coupled device (CCD) camera (ABI 377). In either case the data collection software will collect the signals and store them for subsequent sequence analysis.

PCR products were first purified for sequencing using a QIAQUICK-SPIN PCR PURIFICATION KIT (QIAGEN #28104). The purified PCR products were labeled by adding primers, fluorescently tagged dNTPs and Taq Polymerase FS in an ABI Prism Dye Terminator Cycle Sequencing Kit (PERKIN ELMER/ABI catalog #02154) in a PERKIN ELMER GENEAMP 9600 thermocycler.

The amounts of each component are:

| For Samples | | For Controls | |
|---|---|---|---|
| Reagent | Volume | Reagent | Volume |
| Dye mix | 8.0 µL | PGEM | 2.0 µL |
| Primer (1.6 mM) | 2.0 µL | M13 | 2.0 µL |
| PCR product | 2.0 µL | Dye mix | 8.0 µL |
| sdH2O | 8.0 µL | sdH2O | 8.0 µL |

The thermocycling conditions were:

| Temperature | Time | # of Cycles |
|---|---|---|
| 96° C. | 15 sec. | |
| 50° C. | 5 sec. | 25 |
| 60° C. | 4 min. | |
| 4° C. | Infinity | 1 |

The product was then loaded into a gel and placed into an ABI DNA Sequencer (Models 373A & 377) and run. The sequence obtained was analyzed by comparison to the wild type (reference) sequence within the SEQUENCE NAVIGATOR. When a sequence does not align, it indicates a possible mutation. The DNA sequence was determined in both the forward and reverse direction. All results were provided to a second reader for review.

Heterozygous/homozygous point mutations and polymorphisms must be seen in both strands. Frameshift mutations will be seen in both strands and must have clear double peaks in frame shift regions to be so identified.

PCR Amplification for ASO

The genomic DNA is used as a template to amplify a separate DNA fragment encompassing the site of the mutation to be tested. The 50 µl PCR reaction contained the following components: 1 µl template (100 ng/µl) DNA, 5.0 µl 10× PCR Buffer (PERKIN-ELMER), 2.5 µl dNTP (2 mM each DATP, dCTP, dGTP, dTTP), 2.5 µl Forward Primer (10 µM), 2.5 µl Reverse Primer (10 µM), 0.5 µl (2.5U total) AMPLITAQ® TAQ DNA POLYMERASE or AMPLITAQ GOLD™ DNA POLYMERASE (PERKIN-ELMER), 1.0 to 5.0 µl (25 mM) MgCl$_2$ (depending on the primer) and distilled water (dH$_2$O) up to 50 µl. All reagents for each exon except the genomic DNA can be combined in a master mix and aliquoted into the reaction tubes as a pooled mixture.

For each exon analyzed, the following control PCRs were set up:

(1) "Negative" DNA control (100 ng placental DNA (SIGMA CHEMICAL CO., St. Louis, Mo.)
(2) Three "no template" controls PCR for all exons is performed using the following thermocycling conditions:

| Temperature | Time | Number of Cycles |
|---|---|---|
| 95° C. | 5 min. (AMPLITAQ) or 10 min. (GOLD) | 1 |
| 95° C. | 30 sec. | |
| 55° C. | 30 sec. | 30 cycles |
| 72° C. | 1 min | |
| 72° C. | 5 min. | 1 |
| 4° C. | infinity | 1 |

The quality control agarose gel of PCR amplification was performed as above.

Binding PCR Products to Nylon Membrane

The PCR products are denatured no more than 30 minutes prior to binding the PCR products to the nylon membrane. To denature the PCR products, the remaining PCR reaction (45 µl) and the appropriate positive control mutant gene amplification product are diluted to 200 µl final volume with PCR Diluent Solution (500 mM NaOH, 2.0 M NaCl, 25 mM EDTA) and mixed thoroughly. The mixture is heated to 95° C. for 5 minutes, and immediately placed on ice and held on ice until loaded onto dot blotter, as described below.

The PCR products are bound to 9 cm by 13 cm nylon ZETA PROBE BLOTTING MEMBRANE (BIO-RAD, Hercules, Calif., catalog number 162–0153) using a BIO-RAD dot blotter apparatus. Forceps and gloves are used at all times throughout the ASO analysis to manipulate the membrane, with care taken never to touch the surface of the membrane with bare hands or latex gloves.

Pieces of 3MM filter paper [WHATMAN®, Clifton, N.J.] and nylon membrane are pre-wet in 10×SSC prepared fresh from 20×SSC buffer stock. The vacuum apparatus is rinsed thoroughly with dH₂O prior to assembly with the membrane. 100 μl of each denatured PCR product is added to the wells of the blotting apparatus. Each row of the blotting apparatus contains a set of reactions for a single exon to be tested, including a placental DNA (negative) control, a synthetic oligonucleotide with the desired mutation or a PCR product from a known mutant sample (positive control), and three no template DNA controls.

After applying PCR products, the nylon filter is placed DNA side up on a piece of 3MM filter paper saturated with denaturing solution (1.5M NaCl, 0.5 M NaOH) for 5 minutes. The membrane is transferred to a piece of 3MM filter paper saturated with neutralizing solution (1M Tris-HCl, pH 8, 1.5 M NaCl) for 5 minutes. The neutralized membrane is then transferred to a dry 3MM filter DNA side up, and exposed to ultraviolet light (STRALINKER, STRATAGENE, La Jolla, Calif.) for exactly 45 seconds the fix the DNA to the membrane. This UV crosslinking should be performed within 30 min. of the denaturation/ neutralization steps. The nylon membrane is then cut into strips such that each strip contains a single row of blots of one set of reactions for a single exon.

Hybridizing Labeled Oligonucleotides to the Nylon Membrane

Prehybridization

The strip is prehybridized at 52° C. incubation using the HYBAID® (SAVANT INSTRUMENTS, INC., Holbrook, N.Y.) hybridization oven. 2×SSC (15 to 20 ml) is preheated to 52° C. in a water bath. For each nylon strip, a single piece of nylon mesh cut slightly larger than the nylon membrane strip (approximately 1"×5") is pre-wet with 2×SSC. Each single nylon membrane is removed from the prehybridization solution and placed on top of the nylon mesh. The membrane/mesh "sandwich" is then transferred onto a piece of Parafilm™. The membrane/mesh sandwich is rolled lengthwise and placed into an appropriate HYBAID® bottle, such that the rotary action of the HYBAID® apparatus caused the membrane to unroll. The bottle is capped and gently rolled to cause the membrane/mesh to unroll and to evenly distribute the 2×SSC, making sure that no air bubbles formed between the membrane and mesh or between the mesh and the side of the bottle. The 2×SSC is discarded and replaced with 5 ml TMAC Hybridization Solution, which contained 3 M TMAC (tetramethyl ammoniumchloride—SIGMA T-3411), 100 mM Na₃PO₄ (pH 6.8), 1 mM EDTA, 5×Denhardt's (1% Ficoll, 1% polyvinylpyrrolidone, 1% BSA (fraction V)), 0.6% SDS, and 100 μg/ml Herring Sperm DNA. The filter strips were prehybridized at 52° C. with medium rotation (approx. 8.5 setting on the HYBAID® speed control) for at least one hour. Prehybridization can also be performed overnight.

Labeling Oligonucleotides

The DNA sequences of the oligonucleotide probes used to detect the BRCA1 mutation are as follows (for each mutation, a mutant and a normal oligonucleotide must be labeled):
normal 5'TAT TTT ACA GAT GCA AA 3', SEQ ID NO:3
mutant 5'TAT TTT ACG ATG CAA AC 3', SEQ ID NO:4
normal 5'GAC GGA TGT AAC AAA TA 3', SEQ ID NO:7
mutant 5'GAG ACG GAT AAC AAA TA 3', SEQ ID NO:8
normal 5° CAT GTG GAG CCA TGT GGC ACA AAT ACT 3', SEQ ID NO:9
mutant 5° CAT GTG GAG CCA TGT GGA GCC ATG TGG 3', SEQ ID NO:10
normal 5'TAT TTG GGA AAA CCT AT 3', SEQ ID NO:13
mutant 5'TAT TTG GGA AAC CTA TC 3', SEQ ID NO:14
normal 5'GTA CTG AAT TGC AAA TT 3', SEQ ID NO:17
mutant 5'GTA CTG AAC TGC AAA TT 3', SEQ ID NO:18
normal 5'CAG TAT TTC ATT GGT AC 3', SEQ ID NO:20
mutant 5'CAG TAT TTA ATT GGT AC 3', SEQ ID NO:21
normal 5'GAT AGG TGG TAC ATG CA 3', SEQ ID NO:24
mutant 5'GAT AGG TGA TAC ATG CA 3', SEQ ID NO:25
normal 5'ACA GAA AGG GTC AAC AA 3', SEQ ID NO:28
mutant 5'ACA GAA AGG TCA ACA AA 3', SEQ ID NO:31
normal 5'GTT TGT GTG TGA ACG GA 3', SEQ ID NO:32
mutant 5'GTT TGT GTG GAA CGG AC 3', SEQ ID NO:33
normal 5'CCA CTC TGT ATT CCA CTC CCC TTT GCA G 3', SEQ ID NO:36
mutant 5'CCA CTC TGT ATT CCA CTC TGT ATT CCA C 3', SEQ ID NO:37
normal 5'CAC TTT AAC TAA TCT AA 3', SEQ ID NO:40
mutant 5'CAC TTT AAC AAT CTA AT 3', SEQ ID NO:41
normal 5'TTA TTA TCA TTG AAG AA 3', SEQ ID NO:44
mutant 5'TTA TTA TAA TTG AAG AA 3', SEQ ID NO:45
normal 5'TAA GAA CAC AGA GGA GAA T 3', SEQ ID NO:48
mutant 5'TAA GAA CAC AGG AGA AT 3', SEQ ID NO:49
normal 5'GAA AAG TAT CAG GGT AG 3', SEQ ID NO:50
mutant 5'GAA AAG TAG CAG GGT AG 3', SEQ ID NO:51
normal 5'AAG AGG AAC GGG CTT GG 3', SEQ ID NO:54
mutant 5'AAG AGG ACC GGG CTT GG 3', SEQ ID NO:55

Each labeling reaction contains 2-μl 5× Kinase buffer (or 1 μl of 10× Kinase buffer), 5μl gamma-ATP 32p (not more than one week old), 1 μl T4 polynucleotide kinase, 3 μl oligonucleotide (20 μM stock), sterile H₂O to 10 μl final volume if necessary. The reactions are incubated at 37° C. for 30 minutes, then at 65° C. for 10 minutes to heat inactivate the kinase. The kinase reaction is diluted with an equal volume (10 μl ) of sterile dH₂O (distilled water).

The oligonucleotides are purified on STE MICRO SELECT-D, G-25 spin columns (catalog no. 5303–356769), according to the manufacturer's instructions. The 20 μl synthetic oligonucleotide eluate is diluted with 80 μl dH₂O (final volume=100 μl). The amount of radioactivity in the oligonucleotide sample is determined by measuring the radioactive counts per minute (cpm). The total radioactivity must be at least 2 million cpm. For any samples containing less than 2 million total, the labeling reaction is repeated.

Hybridization with Mutant Oligonucleotides

Approximately 2–5 million counts of the labeled mutant oligonucleotide probe is diluted into 5 ml of TMAC hybridization solution, containing 40 μl of 20 μM stock of unlabeled normal oligonucleotide. The probe mix is preheated to 52° C. in the hybridization oven. The pre-hybridization solution is removed from each bottle and replaced with the probe mix. The filter is hybridized for 1 hour at 52° C. with moderate agitation. Following hybridization, the probe mix is decanted into a storage tube and stored at −20° C. The filter is rinsed by adding approximately 20 ml of 2×SSC+ 0.1% SDS at room temperature and rolling the capped bottle gently for approximately 30 seconds and pouring off the rinse. The filter is then washed with 2×SSC+0.1% SDS at room temperature for 20 to 30 minutes, with shaking.

The membrane is removed from the wash and placed on a dry piece of 3MM WHATMAN filter paper then wrapped in one layer of plastic wrap, placed on the autoradiography film, and exposed for about five hours depending upon a survey meter indicating the level of radioactivity. The film is developed in an automatic film processor.

Control Hybridization with Normal Oligonucleotides

The purpose of this step is to ensure that the PCR products are transferred efficiently to the nylon membrane.

Following hybridization with the mutant oligonucleotide, as described in the Examples above, each nylon membrane is washed in 2×SSC, 0.1% SDS for 20 minutes at 65° C. to melt off the mutant oligonucleotide probes. The nylon strips are then prehybridized together in 40 ml of TMAC hybridization solution for at least 1 hour at 52° C. in a shaking water bath. 2–5 million counts of each of the normal labeled oligonucleotide probes plus 40 μl of 20 μM stock of unlabeled normal oligonucleotide are added directly to the container containing the nylon membranes and the prehybridization solution. The filter and probes are hybridized at 52° C. with shaking for at least 1 hour. Hybridization can be performed overnight, if necessary. The hybridization solution is poured off, and the nylon membrane is rinsed in 2×SSC, 0.1% SDS for 1 minute with gentle swirling by hand. The rinse is poured off and the membrane is washed in 2×SSC, 0.1% SDS at room temperature for 20 minutes with shaking.

The nylon membrane is removed placed on a dry piece of 3MM WHATMAN filter paper. The nylon membrane is then wrapped in one layer of plastic wrap and placed on autoradiography film, and exposure is for at least 1 hour.

For each sample, adequate transfer to the membrane is indicated by a strong autoradiographic hybridization signal. For each sample, an absent or weak signal when hybridized with its normal oligonucleotide, indicates an unsuccessful transfer of PCR product, and it is a false negative. The ASO analysis must be repeated for any sample that did not successfully transfer to the nylon membrane.

Interpreting Results

After hybridizing with mutant oligonucleotides, the results for each exon are interpreted as follows:

TABLE 4A

| Result | Interpretation | Action |
|---|---|---|
|  (+) (−) NT NT NT | All quality controls indicate assay is successful | Record results, dark circles are mutation positive, and all others are negative |
|  (+) (−) NT NT NT | Assay not specific, mutant oligonucleotide hybridizing to normal DNA. | Rewash membrane 30 minutes longer at appropriate temperature and re-expose. |
|  (+) (−) NT NT NT | Mutant oligonucleotide probe is either washed off or did not label well enough, or PCR product is not transferred to membrane efficiently. | Rehybridize with remaining labeled oligonucleotide. If still no signal, perform normal oligonucleotide hyb. as per the Examples to test transfer of PCR to membrane. |
|  (+) (−) NT NT NT | Positive and negative controls indicate assay is successful, but PCR is contaminated. | Perform standard clean up procedures for PCR contamination. Repeat assay. |

After hybridization with normal oligonucleotides, interpret the results as follows:

TABLE 4B

| | | |
|---|---|---|
|  (+) (−) NT NT NT | Results indicate transfer of PCR products to membrane is successful. | Record results. |
|  (+) (−) #1 NT NT NT | Results indicate transfer of patient sample #1 is inefficient. May get false negative from this sample. | This sample will have to be transferred to another membrane and the assay repeated. |

The sample #1 should be lighter than the controls. Patient samples containing a mutation are generally heterozygous and will hybridize to both the normal and mutant oligonucleotide probes.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

All references mentioned herein are incorporated by reference.

We claim:

1. An isolated oligonucleotide that hybridizes to either a normal or a mutant BRCA1 gene selected from the group consisting of:

a first oligonucleotide for detecting a deletion of a nucleotide in intron 6 at nucleotide number 421-2 of a BRCA1 gene sequence, wherein said first oligonucleotide specifically hybridizes to a region encompassing the nucleotide number 421-2 of the BRCA1 gene, a second oligonucleotide for detecting a deletion of two nucleotides at nucleotide number 815 of a BRCA1 gene sequence, wherein said second oligonucleotide specifically hybridizes to a region encompassing the nucleotide number 815 of the BRCA1 gene, a third oligonucleotide for detecting an insertion of 10 nucleotides at nucleotide number 926 of a BRCA1 gene sequence, wherein said third oligonucleotide specifically hybridizes to a region encompassing the nucleotide number 926 of the BRCA1 gene, a fourth oligonucleotide for detecting a deletion of one nucleotide at nucleotide number 1506 of a BRCA1 gene sequence, wherein said fourth oligonucleotide specifically hybridizes to a region encompassing the nucleotide number 1506 of the BRCA1 gene, a fifth oligonucleotide for detecting a mutation of one nucleotide at nucleotide number 2034 of a BRCA1 gene sequence, wherein said fifth oligonucleotide specifically hybridizes to a region encompassing the nucleotide number 2034 of the BRCA1 gene, a sixth oligonucleotide for detecting an amino acid change from serine to a stop codon at codon 770 of a BRCA1 gene sequence, wherein said sixth oligonucleotide specifically hybridizes to a region encompassing the nucleotide number 2428 of the BRCA1 gene, a seventh oligonucleotide for detecting an amino acid change from tryptophan to a stop codon at codon 1508 of a BRCA1 gene sequence, wherein said seventh oligonucleotide specifically hybridizes to a region encompassing the nucleotide number 4643 of the BRCA1 gene, an eighth oligonucleotide for detecting a deletion of one nucleotide at nucleotide number 5053 of a BRCA1 gene sequence, wherein said eighth oligonucleotide specifically hybridizes to a region encompassing the nucleotide number 5053 of the BRCA1 gene, an ninth oligonucleotide for detecting a deletion of one nucleotide at nucleotide number 5210 of a BRCA1 gene sequence, wherein said ninth oligonucleotide specifically hybridizes to a region encompassing the nucleotide number 5210 of the BRCA1 gene, a tenth oligonucleotide for detecting an insertion of 12 nucleotides at nucleotide number 5396+40 in intron 20 of a BRCA1 gene sequence, wherein said tenth oligonucleotide specifically hybridizes to a region encompassing the nucleotide number 5396+40 of the BRCA1 gene, an eleventh oligonucleotide for detecting a deletion of one nucleotide at nucleotide number 5150 of a BRCA1 gene sequence, wherein said eleventh oligonucleotide specifically hybridizes to a region encompassing the nucleotide number 5150 of the BRCA1 gene, a twelfth oligonucleotide for detecting an amino acid change from serine to a stop codon at codon 1262 of a BRCA1 gene sequence, wherein said twelfth oligonucleotide specifically hybridizes to a region encompassing the nucleotide number 3904 of the BRCA1 gene, a thirteenth oligonucleotide for detecting an amino acid change from tyrosine to stop at nucleotide number 903 of a BRCA1 gene sequence, wherein said thirteenth oligonucleotide specifically hybridizes to a region encompassing the nucleotide number 903 of the BRCA1 gene, and a fourteenth oligonucleotide for detecting a detecting an amino acid change from threonine to proline at nucleotide number 4164 of a BRCA1 gene sequence, wherein said fourteenth oligonucleotide specifically hybridizes to a region encompassing the nucleotide number 4164 of the BRCA1 gene.

2. The isolated oligonucleotide according to claim 1 wherein the oligonucleotide detects the presence or absence of an A at nucleotide number 421-2 by specifically hybridizing to the region encompassing nucleotide number 421-2 of the BRCA1 gene.

3. An isolated wild type allele specific oligonucleotide according to claim 2 having the sequence 5'TAT TTT ACA GAT GCA AA 3', SEQ ID NO:3, or the sequence complementary thereto.

4. An isolated mutant allele specific oligonucleotide according to claim 2 having the sequence 5'TAT TTT ACG ATG CAA AC 3', SEQ ID NO:4, or the sequence complementary thereto.

5. The isolated oligonucleotide according to claim 1 wherein the oligonucleotide detects the presence or absence of a TG at nucleotide number 815 by specifically hybridizing to the region encompassing the nucleotide number 815 of the BRCA1 gene.

6. An isolated wild type allele specific oligonucleotide according to claim 5 having the sequence 5'GAC GGA TGT AAC AAA TA 3', SEQ ID NO:7, or the sequence complementary thereto.

7. An isolated mutant allele specific oligonucleotide according to claim 5 having the sequence 5'GAG ACG GAT AAC AAA TA 3', SEQ ID NO:8, or the sequence complementary thereto.

8. The isolated oligonucleotide according to claim 1 wherein the oligonucleotide detects the presence or absence of an insertion at nucleotide number 926 by specifically hybridizing to the region encompassing the nucleotide number 926 of the BRCA1 gene.

9. An isolated wild type allele specific oligonucleotide according to claim 8 having the sequence SEQ ID NO:9, or the sequence complementary thereto.

10. An isolated mutant allele specific oligonucleotide according to claim 8 having the sequence SEQ ID NO:10, or the sequence complementary thereto.

11. The isolated oligonucleotide according to claim 1 wherein the oligonucleotide detects the presence or absence of an A at nucleotide number 1506 by specifically hybridizing to the region encompassing the nucleotide number 1506 of the BRCA1 gene.

12. An isolated wild type allele specific oligonucleotide according to claim 11 having the sequence SEQ ID NO:13, or the sequence complementary thereto.

13. An isolated mutant allele specific oligonucleotide according to claim 11 having the sequence SEQ ID NO:14, or the sequence complementary thereto.

14. The isolated oligonucleotide according to claim 1 wherein the oligonucleotide detects the presence or absence of a nucleotide change at nucleotide number 2034 by specifically hybridizing to the region encompassing the nucleotide number 2034 of the BRCA1 gene.

15. An isolated wild type allele specific oligonucleotide according to claim 14 having the sequence SEQ ID NO:17, or the sequence complementary thereto.

16. An isolated mutant allele specific oligonucleotide according to claim 14 having the sequence SEQ ID NO:18, or the sequence complementary thereto.

17. The isolated oligonucleotide according to claim 1 wherein the oligonucleotide detects the presence or absence of a nucleotide change at nucleotide number 2428 by specifically hybridizing to the region encompassing the nucleotide number 2428 of the BRCA1 gene.

18. An isolated wild type allele specific oligonucleotide according to claim 17 having the sequence SEQ ID NO:20, or the sequence complementary thereto.

19. An isolated mutant allele specific oligonucleotide according to claim 17 having the sequence SEQ ID NO:21, or the sequence complementary thereto.

20. The isolated oligonucleotide according to claim 1 wherein the oligonucleotide detects the presence or absence of a nucleotide change at nucleotide number 4643 by specifically hybridizing to the region encompassing the nucleotide number 4643 of the BRCA1 gene.

21. An isolated wild type allele specific oligonucleotide according to claim 20 having the sequence SEQ ID NO:24, or the sequence complementary thereto.

22. An isolated mutant allele specific oligonucleotide according to claim 20 having the sequence SEQ ID NO:25, or the sequence complementary thereto.

23. The isolated oligonucleotide according to claim 1 wherein the oligonucleotide detects the presence or absence of a G at nucleotide number 5053 by specifically hybridizing to the region encompassing the nucleotide number 5053 of the BRCA1 gene.

24. An isolated wild type allele specific oligonucleotide according to claim 23 having the sequence SEQ ID NO:28, or the sequence complementary thereto.

25. An isolated mutant allele specific oligonucleotide according to claim 23 having the sequence SEQ ID NO:29, or the sequence complementary thereto.

26. The isolated oligonucleotide according to claim 1 wherein the oligonucleotide detects the presence or absence of a T at nucleotide number 5210 by specifically hybridizing to the region encompassing the nucleotide number 5210 of the BRCA1 gene.

27. An isolated wild type allele specific oligonucleotide according to claim 26 having the sequence SEQ ID NO:32, or the sequence complementary thereto.

28. An isolated mutant allele specific oligonucleotide according to claim 26 having the sequence SEQ ID NO:33, or the sequence complementary thereto.

29. The isolated oligonucleotide according to claim 1 wherein the oligonucleotide detects the presence or absence of an insertion at nucleotide number 5396+40 by specifically hybridizing to the region encompassing the nucleotide number 5396+40 of the BRCA1 gene.

30. An isolated wild type allele specific oligonucleotide according to claim 29 having the sequence SEQ ID NO:36, or the sequence complementary thereto.

31. An isolated mutant allele specific oligonucleotide according to claim 29 having the sequence SEQ ID NO:37, or the sequence complementary thereto.

32. The isolated oligonucleotide according to claim 1 wherein the oligonucleotide detects the presence or absence of a deletion at nucleotide number 5150 by specifically hybridizing to the region encompassing the nucleotide number 5150 of the BRCA1 gene.

33. An isolated wild type allele specific oligonucleotide according to claim 32 having the sequence SEQ ID NO:40, or the sequence complementary thereto.

34. An isolated mutant allele specific oligonucleotide according to claim 32 having the sequence SEQ ID NO:41, or the sequence complementary thereto.

35. The isolated oligonucleotide according to claim 1 wherein the oligonucleotide detects the presence or absence of a deletion at nucleotide number 3904 by specifically hybridizing to the region encompassing the nucleotide number 3904 of the BRCA1 gene.

36. An isolated wild type allele specific oligonucleotide according to claim 35 having the sequence SEQ ID NO:44, or the sequence complementary thereto.

37. An isolated mutant allele specific oligonucleotide according to claim 35 having the sequence SEQ ID NO:45, or the sequence complementary thereto.

38. The isolated oligonucleotide according to claim 1 wherein the oligonucleotide detects the presence or absence of a G at nucleotide number 903 by specifically hybridizing to the region encompassing the nucleotide number 903 of the BRCA1 gene.

39. An isolated wild type allele specific oligonucleotide according to claim 38 having the sequence SEQ ID NO:50, or the sequence complementary thereto.

40. An isolated mutant allele specific oligonucleotide according to claim 38 having the sequence SEQ ID NO:51, or the sequence complementary thereto.

41. The isolated oligonucleotide according to claim 1 wherein the oligonucleotide detects the presence or absence of a C at nucleotide number 4164 by specifically hybridizing to the region encompassing the nucleotide number 4164 of the BRCA1 gene.

42. An isolated wild type allele specific oligonucleotide according to claim 41 having the sequence SEQ ID NO:54, or the sequence complementary thereto.

43. An isolated mutant allele specific oligonucleotide according to claim 41 having the sequence SEQ ID NO:55, or the sequence complementary thereto.

44. The isolated oligonucleotide according to claim 1 further comprising a label bound thereto.

45. The isolated oligonucleotide according to claim 44 wherein the label is selected from the group consisting of a radiolabel, a fluorescent label a bioluminescent label, a chemiluminescent label, an enzyme label and a ligand label.

46. An isolated oligonucleotide primer which specifically hybridizes to the BRCA1 gene wherein said primer is selected from the group consisting of:

5'CCA AGG TGT ATG AAG TAT GT 3', SEQ ID NO:5,

5'GTT ATG TTG GCT CCT TGC T 3', SEQ ID NO:6,

5'ACT GTT AGG TTC TGA TGA CT 3', SEQ ID NO:11,

5'ATC ATT TCA GGA GTC TTT TG 3', SEQ ID NO:12,

5'GTG TAG AAC GTG CAG GAT TG 3', SEQ ID NO:38,

5'TCG CCT CAT GTG GTT TTA 3', SEQ ID NO:39,

5'GAA GTA ATT GTA AGC ATC CT 3'SEQ ID NO:42,

5'CAT TTT GTT TCC TCA CTA AG 3'SEQ ID NO:43,

5'CTA AGA ACA CAG AGG AGA A 3', SEQ ID NO:52, and

5'CTA GCT GTG TGA AGG ACT 3', SEQ ID NO:53.

47. An isolated oligonucleotide primer according to claim 46 which is a forward primer comprising the sequence BRCA-1-11F: (SEQ ID NO:5).

48. An isolated oligonucleotide primer according to claim 46 which is a reverse primer comprising the sequence BRCA-1-11R: (SEQ ID NO:6).

49. An isolated oligonucleotide primer according to claim 46 which is a forward primer comprising the sequence BRCA-1-11F: (SEQ ID NO:11).

50. An isolated oligonucleotide primer according to claim 46 which is a reverse primer comprising the sequence BRCA-1-11R: (SEQ ID NO:12).

51. An isolated oligonucleotide primer according to claim 46 which is a forward primer comprising the sequence BRCA-1-17F: (SEQ ID NO:38).

52. An isolated oligonucleotide primer according to claim 46 which is a reverse primer comprising the sequence BRCA-1-17R: (SEQ ID NO:39).

53. An isolated oligonucleotide primer according to claim 46 which is a forward primer comprising the sequence BRCA-1-11F: (SEQ ID NO:42).

54. An isolated oligonucleotide primer according to claim 46 which is a reverse primer comprising the sequence BRCA-1-11R: (SEQ ID NO:43).

55. A pair of isolated oligonucleotide primers which specifically hybridize to the BRCA1 gene, wherein the pair is:

a primer having the sequence BRCA-1-11F: (SEQ ID NO:5) and a primer having the sequence BRCA-1-11R: (SEQ ID NO:6);

a primer having the sequence BRCA-1-11F: (SEQ ID NO:11) and a primer having the sequence BRCA-1-11R: (SEQ ID NO:12);

a primer having the sequence BRCA-1-17F: (SEQ ID NO:38) and a primer having the sequence BRCA-1-17R: (SEQ ID NO:39);

a primer having the sequence BRCA-1-11F: (SEQ ID NO:42) and a primer having the sequence BRCA-1-11R: (SEQ ID NO:43); or a primer having the sequence BRCA-1-11F: (SEQ ID NO:52) and a primer having the sequence BRCA-1-11R: (SEQ ID NO:53).

56. The pair of primers according to claim 55 wherein said pair comprises a primer having the sequence BRCA-1-11F: (SEQ ID NO:5) and a primer comprising the sequence BRCA-1-11R: (SEQ ID NO:6).

57. The pair of primers according to claim 55 wherein said pair comprises a primer having the sequence BRCA-1-11F: (SEQ ID NO:11) and a primer comprising the sequence BRCA-1-11R: (SEQ ID NO:12).

58. The pair of primers according to claim 55 wherein said pair comprises a primer having the sequence BRCA-1-17F: (SEQ ID NO:38) and a primer comprising the sequence BRCA-1-17R: (SEQ ID NO:39).

59. The pair of primers according to claim 55 wherein said pair comprises a primer having the sequence BRCA-1-11F: (SEQ ID NO:42) and a primer comprising the sequence BRCA-1-11R: (SEQ ID NO:43).

60. The pair of primers according to claim 55 wherein said pair comprises a primer having the sequence BRCA-1-11F: (SEQ ID NO:52) and a primer comprising the sequence BRCA-1-11R: (SEQ ID NO:53).

61. The pair of isolated oligonucleotide primers according to claim 55, wherein each primer is bound to a label.

62. The pair of primers according to claim 61 wherein each of said labels is selected from the group consisting of a radiolabel, a fluorescent label a bioluminescent label a chemiluminescent label, an enzyme label and a ligand label.

63. The isolated oligonucleotide primer according to claim 46 bound to a label.

64. The primer according to claim 63 wherein said label is selected from the group consisting of a radiolabel, a fluorescent label a bioluminescent label a chemiluminescent label, an enzyme label and a ligand label.

65. A method for determining the presence or absence of a sequence variation in a BRCA2 gene sample, comprising:
(a) performing an allele specific detection assay for the presence or absence of one or more predetermined sequence variations; and
(b) determining the presence or absence of a predetermined sequence variation in the BRCA1 gene sample at nucleotide number 421-2, 815, 926, 1506, 2034, 2428, 4643, 5053, 5210, 5396+40, 5150, 3904, 903, 4164 or its complementary gene sequence.

66. The method according to claim 65 wherein the predetermined sequence variation is IVS6-2delA, 815delTG, 926ins10, 1506delA, T2034C, C2428A, G4643A, 5053delG, 5210delT, IVS20+40ins12, 5150delT, C3904A, T903G or A4164C.

67. The method of claim 65 wherein the allele specific detection assay is performed as part of a multiplex amplification assay format.

68. The method of claim 65 wherein the allele specific sequence-based assay is performed using a dot blot format, reverse dot blot format, a multiplex allele specific diagnostic assay format, or a chip array format.

69. The method according to claim 65 further comprising
(c) performing an allele specific detection assay for the presence or absence of one or more reference sequences without the predetermined sequence variations.

70. The method according to claim 69 wherein said reference sequence is a BRCA1 coding sequence.

71. The method according to claim 69 wherein said reference sequence is a BRCA1 genomic sequence.

72. The method according to claim 69 wherein said reference sequence is one or more exons of the BRCA1 gene.

73. A chip array having "n" elements for performing allele specific sequence-based techniques comprising;
a solid phase chip and
oligonucleotides having "n" different nucleotide sequences,
wherein "n" is an integer greater than one, p1 wherein said oligonucleotides are bound to said solid phase chip in a manner which permits said oligonucleotides to effectively hybridize to complementary oligonucleotides or polynucleotides,
wherein oligonucleotides having different nucleotide sequence are bound to said solid phase chip at different locations so that a particular location on said solid phase chip exclusively binds oligonucleotides having a specific nucleotide sequence, and
wherein at least one oligonucleotide is an oligonucleotide according to claim 1.

74. A method of detecting a predisposition or higher susceptibility to cancer in an individual, comprising:
(a) digesting DNA from said individual with a restriction endonuclease;
(b) separating DNA fragments obtained from said digestion;
(c) detecting a DNA fragment containing a sequence variation at nucleotide number 421-2, 815, 926, 1506, 2034, 2428, 4643, 5053, 5210, 5396+40, 5150, 3904, 903 or 4164 of a BRCA1 gene sequence or the complementary sequence thereof by sequencing;

(d) analyzing the DNA fragment sequence for the presence of a sequence variation at nucleotide number 421-2, 815, 926, 1506, 2034, 2428, 4643, 5053, 5210, 5396+40, 5150, 3904, 903 or 4164 of the BRCA1 gene sequence, wherein the presence of a sequence variation indicates a predisposition or higher susceptibility to cancer.

75. A method according to claim 74 further comprising amplifying said DNA fragments prior to sequencing.

76. A method according to claim 74 wherein the sequence variation is amplified prior to detection by sequencing with an oligonucleotide primer having a sequence comprising;
5'CAC AAC AAA GAG CAT ACA TAG GG 3', SEQ ID NO:1
5'TCG GGT TCA CTC TGT AGA AG 3', SEQ ID NO:2
5'CCA AGG TGT ATG AAG TAT GT 3', SEQ ID NO:5
5'GTT ATG TTG GCT CCT TGC T 3', SEQ ID NO:6
5'ACT GTT AGG TTC TGA TGA CT 3', SEQ ID NO:11
5'ATC ATT TCA GGA GTC TTT TG 3', SEQ ID NO:12
5'GTA TAA GCA ATA TGG AAC TCG A 3', SEQ ID NO:15
5'TTA AGT TCA CTG GTA TTT GAA CA 3', SEQ ID NO:16
5'TGG AAC AAC CAT GAA TTA GTC 3', SEQ ID NO:19
5'TGG CTG CCC AGG AAG TAT G 3', SEQ ID NO:22
5'AAC CAG AAT ATC TTT ATG TAG GA 3', SEQ ID NO:23
5'AAT TCT TAA CAG AGA CCA GAA C 3', SEQ ID NO:26
5'AAA ACT CTT TCC AGA ATG TTG T 3', SEQ ID NO:27
5'GGC TCT TTA GCT TCT TAG GAC 3', SEQ ID NO:30,
5'GAG ACC ATT TTC CCA GCA TC 3', SEQ ID NO:31,
5'ATA TGA CGT GTC TGC TCC AC 3', SEQ ID NO:34,
5'GGG AAT CCA AAT TAC ACA GC 3', SEQ ID NO:35,
5'GTG TAG AAC GTG CAG GAT TG 3', SEQ ID NO:38,
5'TCG CCT CAT GTG GTT TTA 3', SEQ ID NO:39,
5'GAA GTA ATT GTA AGC ATC CT 3', SEQ ID NO:42,
5'CAT TTT GTT TCC TCA CTA AG 3', SEQ ID NO:43,
5'CTA AGA ACA CAG AGG AGA A 3', SEQ ID NO:52, or
5'CTA GCT GTG TGA AGG ACT 3', SEQ ID NO:53.

77. A method according to claim 76 wherein said oligonucleotide primer is labeled with a radiolabel, a fluorescent label a bioluminescent label, a chemiluminescent label, an enzyme label, or a ligand label.

78. A method of detecting a predisposition or higher susceptibility to cancer in an individual, comprising;
(a) digesting DNA from said individual with a restriction endonuclease;
(b) separating DNA fragments obtained from said digestion;
(c) hybridizing a DNA fragment with an allele specific oligonucleotide having a nucleotide sequence capable of hybridizing to and identifying a sequence variation at nucleotide position 421-2, 815, 926, 1506, 2034, 2428, 4643, 5053, 5210, 5396+40, 5150, 3904, 903 or 4164 of the BRCA1 gene sequence or its complementary gene sequence,
(d) correlating the presence or absence of said sequence variation with the respective presence or absence of the BRCA1 gene, thereby determining a predisposition or higher susceptibility to cancer.

79. A method according to claim 74 wherein said allele specific oligonucleotide is selected from the group consisting of:

5'TAT TTT ACA GAT GCA AA 3', SEQ ID NO:3,
5'TAT TTT ACG ATG CAA AC 3', SEQ ID NO:4,
5'GAC GGA TGT AAC AAA TA 3', SEQ ID NO:7,
5'GAG ACG GAT AAC AAA TA 3', SEQ ID NO:8,
5'CAT GTG GAG CCA TGT GGC ACA AAT ACT 3', SEQ ID NO:9,
5'CAT GTG GAG CCA TGT GGA GCC ATG TGG 3', SEQ ID NO:10,
5'TAT TTG GGA AAA CCT AT 3', SEQ ID NO:13,
5'TAT TTG GGA AAC CTA TC 3', SEQ ID NO:14,
5'GTA CTG AAT TGC AAA TT 3', SEQ ID NO:17,
5'GTA CTG AAC TGC AAA TT 3', SEQ ID NO:18,
5'CAG TAT TTC ATT GGT AC 3', SEQ ID NO:20,
5'CAG TAT TTA ATT GGT AC 3', SEQ ID NO:21,
5'GAT AGG TGG TAC ATG CA 3', SEQ ID NO:24,
5'GAT AGG TGA TAC ATG CA 3', SEQ ID NO:25,
5'ACA GAA AGG GTC AAC AA 3', SEQ ID NO:28,
5'ACA GAA AGG TCA ACA AA 3', SEQ ID NO:29,
5'GTT TGT GTG TGA ACG GA 3', SEQ ID NO:32,
5'GTT TGT GTG GAA CGG AC 3', SEQ ID NO:33,
5'CCA CTC TGT ATT CCA CTC CCC TTT GCA G 3', SEQ ID NO:36,
5'CCA CTC TGT ATT CCA CTC TGT ATT CCA C 3', SEQ ID NO:37,
5'CAC TTT AAC TAA TCT AA 3', SEQ ID NO:40,
5'CAC TTT AAC AAT CTA AT 3', SEQ ID NO:41,
5'TTA TTA TCA TTG AAG AA 3', SEQ ID NO:44,
5'TTA TTA TAA TTG AAG AA 3', SEQ ID NO:45,
5'GAA AAG TAT CAG GGT AG 3', SEQ ID NO:50
5'GAA AAG TAG CAG GGT AG 3', SEQ ID NO:51
5'AAG AGG AAC GGG CTT GG 3', SEQ ID NO:54
5'AAG AGG ACC GGG CTT GG 3', SEQ ID NO:55 and oligonucleotides complementary thereto.

80. A method according to claim 78 further comprising amplifying said DNA fragments prior to sequencing.

81. A method according to claim 78 wherein said oligonucleotide is labeled with a radiolabel, a fluorescent label a bioluminescent label, a chemiluminescent label, an enzyme label, or a ligand label.

82. A kit comprising a carrier means being compartmentalized to receive in close confinement one or more container means, and at least one container means, wherein at least one container means contains the oligonucleotide of claim 1.

83. The kit acording to claim 75 further comprising at least one container means containing the oligonucleotide primer of claim 50.

84. The kit according to claim 82 further comprising at least one container means containing the pair of oligonucleotide primers of claim 55.

85. A kit comprising a carrier means being compartmentalized to receive in close confinement one or more container means, and at least one container means, wherein at least one container means contains the oligonucleotide primer of claim 46.

86. A kit comprising a carrier means being compartmentalized to receive in close confinement one or more container means, and at least one container means, wherein at least one container means contains the pair of oligonucleotide primers of claim 55.

87. An isolated DNA sequence comprising DNA coding for or complementary to at least a part of a BRCA1 gene containing at least one mutation from the list: IVS6-2delA, 815delTG, 926ins10, 1506delA, T2034C, C2428A, G4643A, 5053delG, 5210delT, IVS20+40ins12, 5150delT, C3904A, T903G or A4164C.

88. A vector comprising the isolated DNA sequence according to claim 87 linked to a vector by at least one of the termini of the isolated DNA sequence.

89. An isolated DNA sequence according to claim 87, wherein the isolated DNA sequence contains the sequence of or a sequence complementary to at least one of the following: SEQ ID NO:4, SEQ ID NO:8, SEQ ID NO:10, SEQ ID NO:14:, SEQ ID NO:18, SEQ ID NO:21, SEQ ID NO:25, SEQ ID NO:29, SEQ ID NO:33, SEQ ID NO:37, SEQ ID NO:41, SEQ ID NO:45, SEQ ID NO:51, or SEQ ID NO:55.

90. A vector comprising the isolated DNA sequence according to claim 89 linked to a vector by at least one of the termini of the isolated DNA sequence.

91. A method of determining whether a mutation is present in a BRCA1 gene comprising sequencing at least a portion of the BRCA1 gene containing either:

the sequence of or the sequence complementary to SEQ ID NO:4, SEQ ID NO:8, SEQ ID NO:10, SEQ ID NO:14, SEQ ID NO:18, SEQ ID NO:21, SEQ ID NO:25, SEQ ID NO:29, SEQ ID NO:33, SEQ ID NO:37, SEQ ID NO:41, SEQ ID NO:45, SEQ ID NO:51, SEQ ID NO:55 or at least one mutation from the list: IVS6-2delA, 815delTG, 926ins10, 1506delA, T2034C, C2428A, G4643A, 5053delG, 5210delT, IVS20+40ins12, 5150delT, C3904A, T903G and A4164C.

* * * * *

UNITED STATES PATENT AND TRADEMARK OFFICE
CERTIFICATE OF CORRECTION

PATENT NO. : 6,083,698

DATED : July 4, 2000

INVENTOR(S) : Olson et al.

It is certified that error appears in the above-identified patent and that said Letters Patent is hereby corrected as shown below:

Column 71, line 6,

"BRCA2" should read --BRCA1--;

Column 71, line 44,

"p1" should be deleted;

Column 73, line 3,

"claim 74" should read --claim 78--;

Column 74, line 34

"or" should read --and--.

Signed and Sealed this

Seventeenth Day of April, 2001

Attest:

NICHOLAS P. GODICI

Attesting Officer  Acting Director of the United States Patent and Trademark Office